(12) United States Patent
Zonana et al.

(10) Patent No.: US 10,392,181 B2
(45) Date of Patent: Aug. 27, 2019

(54) SMART CAP SYSTEM

(71) Applicant: COMPLIANCE MEDS TECHNOLOGIES, LLC, North Miami Beach, FL (US)

(72) Inventors: Moses Zonana, Hallandale Beach, FL (US); Ben Way, Ft. Lauderdale, FL (US); Daniel Garcia, Miami, FL (US); Rodrigo Ferreira, Miami, FL (US); Werner Blumenthal, Miami, FL (US)

(73) Assignee: COMPLIANCE MEDS TECHNOLOGIES, LLC, Miami, FL (US)

( * ) Notice: Subject to any disclaimer, the term of this patent is extended or adjusted under 35 U.S.C. 154(b) by 252 days.

(21) Appl. No.: 14/255,309

(22) Filed: Apr. 17, 2014

(65) Prior Publication Data

US 2014/0305963 A1   Oct. 16, 2014

Related U.S. Application Data

(63) Continuation of application No. 13/364,841, filed on Feb. 2, 2012, now Pat. No. 8,727,180.

(51) Int. Cl.
*B65D 83/04* (2006.01)
*A61J 7/00* (2006.01)
(Continued)

(52) U.S. Cl.
CPC ........ *B65D 83/0409* (2013.01); *A61J 7/0076* (2013.01); *A61J 7/0409* (2013.01);
(Continued)

(58) Field of Classification Search
CPC ......... B65D 83/0409; B65D 2101/0015; A61J 7/0076; A61J 7/0409; A61J 7/0481;
(Continued)

(56) References Cited

U.S. PATENT DOCUMENTS 2,851,191 A   9/1958   Semsch
2,923,436 A   2/1960   Koehn
(Continued)

FOREIGN PATENT DOCUMENTS

DE   202 16 870   1/2003
EP   1 503 947    2/2005
(Continued)

OTHER PUBLICATIONS

"eCAP . . . the smart cap that enhances medication adherence", Information Mediary Corporation (IMC) and Affiliates, 2011, May 30, 2012, pp. 1-2.
(Continued)

*Primary Examiner* — Michael Collins
(74) *Attorney, Agent, or Firm* — Leason Ellis LLP

(57) ABSTRACT

A medicine container cap for use with a bottle containing a plurality of pills includes a casing having a pill dispensing opening. A pill dispensing track assembly is removably coupled to the casing and includes a pill ramp for delivering pills to the pill dispensing opening and an insert that includes a pill dispenser slot that receives pills from the pill ramp and is open to the pill dispensing opening. The insert is detachably from the pill ramp and is insertable through an opening in the casing for being attached to the pill ramp. The pill ramp includes an adjustable member that modifies a characteristic of the pill ramp based on at least one characteristic of the insert that is selected, inserted through the opening in the casing and coupled to the pill ramp.

31 Claims, 25 Drawing Sheets

(51) Int. Cl.
*A61J 7/04* (2006.01)
*G06F 19/00* (2018.01)
*A61J 1/03* (2006.01)

(52) U.S. Cl.
CPC .......... *A61J 7/0436* (2015.05); *A61J 7/0481* (2013.01); *G06F 19/3462* (2013.01); *A61J 1/03* (2013.01); *A61J 7/0418* (2015.05); *A61J 7/0445* (2015.05); *A61J 7/0454* (2015.05); *A61J 2200/30* (2013.01); *B65D 2101/0015* (2013.01)

(58) Field of Classification Search
CPC ...... A61J 7/0436; A61J 7/0418; A61J 7/0454; A61J 7/0445; A61J 1/03; G06F 19/3462
USPC ............. 221/241, 246–247, 194–196, 288, 9
See application file for complete search history.

(56) References Cited

U.S. PATENT DOCUMENTS

| | | | |
|---|---|---|---|
| 3,224,634 A * | 12/1965 | Semsch | B65D 83/0409 221/299 |
| 3,601,250 A | 8/1971 | Merila | |
| 3,991,908 A | 11/1976 | Thomas et al. | |
| 4,150,766 A * | 4/1979 | Westendorf | B65D 83/0409 221/112 |
| 4,405,045 A | 9/1983 | Villa-Real | |
| 4,611,727 A | 9/1986 | Graff | |
| 4,662,537 A | 5/1987 | Wolf et al. | |
| 4,869,392 A | 9/1989 | Moulding, Jr. et al. | |
| 4,939,705 A | 7/1990 | Hamilton et al. | |
| 5,011,032 A | 4/1991 | Rollman | |
| 5,014,798 A | 5/1991 | Glynn | |
| 5,018,644 A * | 5/1991 | Hackmann | B65D 83/0409 221/152 |
| 5,110,008 A | 5/1992 | Moulding et al. | |
| 5,148,944 A | 9/1992 | Kaufman et al. | |
| 5,213,232 A * | 5/1993 | Kraft | B65D 83/0409 198/657 |
| 5,233,571 A | 8/1993 | Wirtschafter | |
| 5,239,491 A | 8/1993 | Mucciacciaro | |
| 5,313,439 A | 5/1994 | Albeck | |
| 5,347,453 A | 9/1994 | Maestre | |
| 5,472,113 A | 12/1995 | Shaw | |
| 5,571,258 A * | 11/1996 | Pearson | A61J 7/0084 221/211 |
| 5,583,831 A | 12/1996 | Churchill et al. | |
| 5,609,268 A | 3/1997 | Shaw | |
| 5,616,299 A * | 4/1997 | Walker | B01L 99/00 221/197 |
| 5,623,242 A | 4/1997 | Dawson, Jr. et al. | |
| 5,646,912 A | 7/1997 | Cousin | |
| 5,751,660 A | 5/1998 | Chappell | |
| 5,751,661 A | 5/1998 | Walters | |
| 5,752,620 A | 5/1998 | Pearson | |
| 5,791,515 A | 8/1998 | Khan et al. | |
| 5,805,051 A | 9/1998 | Herrmann et al. | |
| 5,845,255 A | 12/1998 | Mayaud | |
| 5,884,806 A | 3/1999 | Boyer et al. | |
| 5,915,589 A | 6/1999 | Lim | |
| 5,953,288 A | 9/1999 | Chappell | |
| 5,971,594 A | 10/1999 | Sahai et al. | |
| 5,995,938 A | 11/1999 | Whaley | |
| 6,018,289 A | 1/2000 | Sekura et al. | |
| 6,138,865 A | 10/2000 | Gilmore | |
| 6,142,337 A * | 11/2000 | Schreckenberg | A61J 1/03 221/263 |
| 6,168,563 B1 | 1/2001 | Brown | |
| 6,194,995 B1 * | 2/2001 | Gates | A61J 7/0481 206/531 |
| 6,201,768 B1 | 3/2001 | de Meyer et al. | |
| 6,220,480 B1 | 4/2001 | Stankus et al. | |
| 6,229,431 B1 | 5/2001 | Weiner | |
| 6,263,259 B1 | 7/2001 | Bartur | |
| 6,299,019 B1 | 10/2001 | Leight | |
| 6,324,123 B1 | 11/2001 | Durso | |
| 6,335,907 B1 | 1/2002 | Momich et al. | |
| 6,427,865 B1 | 8/2002 | Stillwell et al. | |
| 6,488,174 B1 | 12/2002 | Cho | |
| 6,507,275 B2 | 1/2003 | Romano et al. | |
| 6,510,962 B1 | 1/2003 | Lim | |
| 6,529,446 B1 | 3/2003 | de la Huerga | |
| 6,545,592 B2 | 4/2003 | Weiner | |
| 6,574,165 B2 | 6/2003 | Sharma et al. | |
| 6,592,005 B1 | 7/2003 | Coughlin et al. | |
| 6,594,549 B2 | 7/2003 | Siegel | |
| 6,604,650 B2 | 8/2003 | Sagar | |
| 6,667,936 B1 | 12/2003 | Ditzig | |
| 6,702,146 B2 | 3/2004 | Varis | |
| 6,707,763 B2 | 3/2004 | Osberg et al. | |
| 6,751,730 B1 | 6/2004 | Walker et al. | |
| 6,988,634 B2 | 1/2006 | Varis | |
| 7,072,738 B2 | 7/2006 | Bonney et al. | |
| 7,073,685 B1 | 7/2006 | Giraud et al. | |
| 7,081,807 B2 | 7/2006 | Lai | |
| 7,097,068 B2 | 8/2006 | Limback et al. | |
| 7,107,122 B1 * | 9/2006 | Whyte | A61J 7/0481 221/12 |
| 7,139,639 B2 | 11/2006 | Broussard et al. | |
| 7,147,130 B1 | 12/2006 | Clark et al. | |
| 7,158,011 B2 | 1/2007 | Brue | |
| 7,204,391 B2 | 4/2007 | Toker | |
| 7,213,721 B2 | 5/2007 | Abdulhay et al. | |
| 7,295,889 B2 | 11/2007 | Lahteenmaki | |
| 7,295,890 B2 | 11/2007 | Jean-Pierre | |
| 7,330,101 B2 | 2/2008 | Sekura | |
| 7,359,765 B2 | 4/2008 | Varvarelis et al. | |
| 7,366,675 B1 | 4/2008 | Walker et al. | |
| RE40,453 E | 8/2008 | Lasher et al. | |
| 7,408,843 B2 | 8/2008 | Brandon | |
| 7,418,961 B2 | 9/2008 | Jones et al. | |
| 7,444,203 B2 | 10/2008 | Rosenblum | |
| 7,469,820 B2 | 12/2008 | Rosenblum | |
| 7,471,993 B2 | 12/2008 | Rosenblum | |
| D592,507 S | 5/2009 | Wachman et al. | |
| 7,545,257 B2 | 6/2009 | Brue | |
| 7,554,434 B1 | 6/2009 | Gifford et al. | |
| 7,574,370 B2 | 8/2009 | Mayaud | |
| 7,606,723 B2 | 10/2009 | Mayaud | |
| 7,624,894 B2 | 12/2009 | Gerold et al. | |
| 7,715,277 B2 | 5/2010 | de la Huerga | |
| 7,719,927 B2 | 5/2010 | Robinson et al. | |
| 7,735,681 B2 | 6/2010 | Handfield et al. | |
| 7,739,124 B1 | 6/2010 | Walker et al. | |
| 7,796,472 B2 | 9/2010 | Brandon | |
| 7,801,745 B2 | 9/2010 | Walker et al. | |
| 7,832,591 B2 | 11/2010 | Karwacki, Jr. et al. | |
| 7,844,361 B2 | 11/2010 | Jean-Pierre | |
| 7,860,603 B2 | 12/2010 | Handfield et al. | |
| 7,877,268 B2 | 1/2011 | Kulkarni | |
| 7,878,350 B2 | 2/2011 | Ramoundos | |
| 7,896,192 B2 | 3/2011 | Conley et al. | |
| 7,907,477 B2 | 3/2011 | Puzia | |
| 7,928,835 B1 | 4/2011 | Jovanov et al. | |
| 7,988,016 B2 * | 8/2011 | Klein | B65D 83/0409 221/1 |
| 8,032,397 B2 | 10/2011 | Lawless | |
| 8,033,424 B2 | 10/2011 | Rosenblum | |
| 8,055,509 B1 | 11/2011 | Walker et al. | |
| 8,056,760 B2 | 11/2011 | Moran, Jr. et al. | |
| 8,060,246 B2 | 11/2011 | Berg | |
| 8,068,931 B2 | 11/2011 | Tran et al. | |
| 8,069,056 B2 | 11/2011 | Walker et al. | |
| D650,986 S | 12/2011 | Brady et al. | |
| 8,091,719 B2 | 1/2012 | Wu | |
| 8,138,939 B2 | 3/2012 | Manning et al. | |
| 8,149,096 B2 | 4/2012 | Metry et al. | |
| 8,152,020 B2 | 4/2012 | Flowers et al. | |
| 8,154,390 B2 | 4/2012 | Heath et al. | |
| 8,165,896 B2 | 4/2012 | Jung et al. | |
| 8,727,180 B2 * | 5/2014 | Zonana | B65D 83/0409 221/241 |

(56) References Cited

U.S. PATENT DOCUMENTS

| | | |
|---|---|---|
| 2002/0093429 A1 | 7/2002 | Matsushita et al. |
| 2002/0104848 A1 | 8/2002 | Burrows et al. |
| 2003/0183642 A1* | 10/2003 | Kempker, Sr. ........ A61J 7/0084 221/2 |
| 2004/0124204 A1 | 7/2004 | Giraud |
| 2005/0029154 A1 | 2/2005 | Kahn et al. |
| 2006/0071011 A1* | 4/2006 | Varvarelis ............. A61J 7/0481 221/9 |
| 2006/0207996 A1 | 9/2006 | Marteau et al. |
| 2007/0014191 A1 | 1/2007 | Brandon |
| 2007/0016443 A1 | 1/2007 | Wachman et al. |
| 2008/0142533 A1 | 6/2008 | Handfield et al. |
| 2009/0134181 A1 | 5/2009 | Wachman et al. |
| 2009/0192648 A1 | 7/2009 | Namineni et al. |
| 2009/0218363 A1* | 9/2009 | Terzini ...................... A61J 7/02 221/4 |
| 2009/0259336 A1 | 10/2009 | Ratnakar |
| 2010/0006589 A1 | 1/2010 | Klein |
| 2010/0100237 A1 | 4/2010 | Ratnakar |
| 2010/0100391 A1 | 4/2010 | Daya et al. |
| 2010/0270257 A1* | 10/2010 | Wachman ........... G06F 19/3462 215/228 |
| 2010/0305967 A1 | 12/2010 | Daya et al. |
| 2010/0305975 A1 | 12/2010 | Daya et al. |
| 2011/0119090 A1 | 5/2011 | Lazar |
| 2011/0164559 A1 | 7/2011 | Bamidele |
| 2011/0284415 A1 | 11/2011 | Balakier et al. |
| 2012/0101630 A1 | 4/2012 | Daya et al. |
| 2013/0200033 A1 | 8/2013 | Zonana et al. |

FOREIGN PATENT DOCUMENTS

| | | |
|---|---|---|
| JP | S57-013034 | 1/1982 |
| JP | H04-279423 | 10/1992 |
| JP | 2007-501174 | 1/2007 |
| WO | WO 2003/001337 | 1/2003 |
| WO | WO 03/097483 | 11/2003 |
| WO | WO 2011/011114 | 1/2011 |
| WO | WO 2011/154018 | 12/2011 |

OTHER PUBLICATIONS

Watters, Joanne, "eCAP . . . the smart cap that enhances medication adherence, Key Features", Information Mediary Corporation, p. 1.

"eCAP . . . the smart cap that enhances medication adherence, Technical Specifications", Information Mediary Corporation (IMC) and Affiliates, p. 1.

"Introducing GlowCaps", Vitality Inc. 2010, May 30, 2012 p. 1 of 1.

"Introducing GlowCaps, How GlowCaps Work", Vitality Inc. 2010, May 30, 2012 p. 1 of 1.

* cited by examiner

US 10,392,181 B2

SMART CAP SYSTEM

CROSS REFERENCE TO RELATED APPLICATION

The present application is a continuation of U.S. patent application Ser. No. 13/364,841, filed Feb. 2, 2012, which is hereby incorporated by reference in its entirety.

TECHNICAL FIELD

The present invention relates to medication compliance management and in particular, to a medication dispensing device that controls medication dispensing based on compliance to the prescribed dosage and also keeps a record of the dispensing history.

BACKGROUND

The majority of medicines and drugs require administration in a series of doses at specific times over a period of time for increased effectiveness. Outside of a hospital or clinic setting, this usually requires the patient or an individual caring for the patient to be responsible for keeping track of the medication in question. However, a frequent problem is that the patient or the individual caring for the patient errs in the administration of the medicine. Patients may forget to take a dose of their medication, be tardy in taking a dose, or forget entirely to take a dose and/or take a second dose too soon, etc.

In addition, with some drugs, such as controlled substances (e.g., oxycodone), there is a risk that patient may not follow the dosage instructions as a result of a drug addiction and/or there is even a risk that a patient may illegally sell and distribute some of the pills and then subsequently allege that the pills are misplaced, lost, or stolen, etc.

A number of approaches to solving the above problems have been proposed and embodied in different devices. In particular, there are a number of devices that include a pill case or box with a timer or alarm to alert the patient that a certain time period has passed and that the medication should be taken. Also, these simple alarms provide no means to ensure or check compliance with administration of the medication. Moreover, if the patient fails to take the medication at the prescribed time, the patient is likely to fail to reset the timer or alarm.

In addition, existing products are not particularly suited to handle different sized and different shaped pills but instead, typically require a new entire dispensing device for different categories of pills. This is costly and also overly complex.

SUMMARY

In accordance with one embodiment, a medicine container cap for use with a bottle containing a plurality of pills includes a casing having a pill dispensing opening. The casing is configured to securely attach to the bottle and represent a cap structure that closes off the bottle. The cap also includes a door member coupled to the casing and movable between an idle position, a load position and dispensing position in which the pill dispensing opening is open and one pill is released. A pill dispensing track assembly is removably coupled to the casing and includes a pill ramp for delivering pills to the pill dispensing opening and an insert that includes a pill dispenser slot that receives pills from the pill ramp and is open to the pill dispensing opening. The pill ramp is coupled to the casing and for insertion into the bottle to contact pills therein. The insert is detachably from the pill ramp and is insertable through an opening in the casing for being attached to the pill ramp. The pill ramp includes an adjustable member that modifies a characteristic of the pill ramp based on at least one characteristic of the insert that is selected, inserted through the opening in the casing and coupled to the pill ramp.

In one embodiment, the characteristic of the pill ramp includes a height of at least a tunnel portion defined between the adjustable member and the pill ramp proximate the pill dispensing slot. A height of the tunnel controls an orientation in which the pills can slide along pill ramp into the pill dispensing slot and the characteristic of the insert is a height thereof.

According to one embodiment, a medicine container cap for use with a bottle containing a plurality of pills includes a casing having a pill dispensing opening. The casing is configured to securely attach to the bottle and represents a cap structure that closes off the bottle. The cap also includes a door member coupled to the casing and movable between an idle position, a load position and dispensing position in which the pill dispensing opening is open and one pill is released. A pill dispensing track assembly is provided and is removably coupled to the casing and includes a pill ramp for delivering pills to the pill dispensing opening. The pill ramp includes a central shaft and a helical shaped ramp extending about the central shaft. The pill dispensing track assembly also includes an insert that includes a pill dispenser slot that receives pills from the pill ramp and is open to the pill dispensing opening. The pill ramp is coupled to the casing and for insertion into the bottle to contact pills therein. The insert is detachably from the pill ramp and insertable through an opening in the casing for being attached to the pill ramp resulting in the pill ramp being in registration with the pill dispensing slot.

An adjustable member is provided and has a first portion attached to the central shaft and a second portion that is attached to the insert. The adjustable member is disposed between ramp portions of the pill ramp. The adjustable member includes an underside surface that faces an underlying ramp portion with a pill space being defined between the adjustable member and the underlying ramp portion. The adjustable member is adjustable along a vertical axis so as to alter dimensions of the pill space. In accordance with the present invention, there is a direct correspondence between a height of the insert and the position of the adjustable member along the central shaft.

These and other aspects, features and advantages shall be apparent from the accompanying drawings and description of certain embodiments of the invention.

DETAILED DESCRIPTION OF CERTAIN EMBODIMENTS OF THE INVENTION

Figure 1:
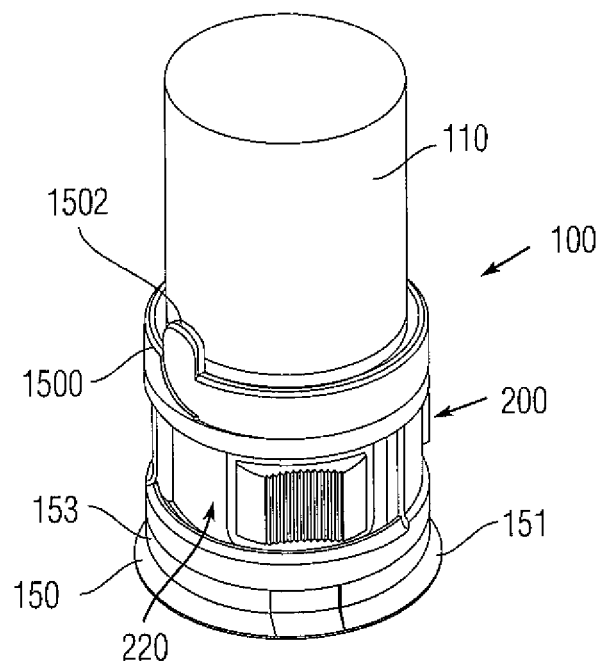
FIG. 1 is a top and side perspective view of a pill dispenser device according to the present invention coupled to a pill bottle.
Figure 2:
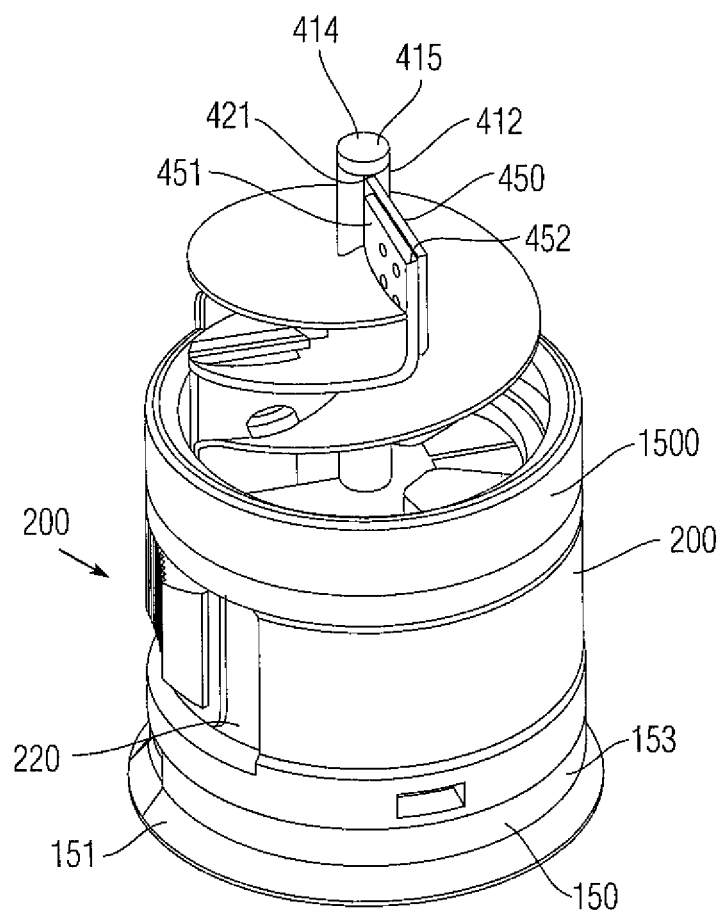
FIG. 2 is a top and side perspective view of bottom components of the pill dispenser device of FIG. 1 including a base, casing and pill dispensing mechanism shown without the pill bottle.
Figure 3:
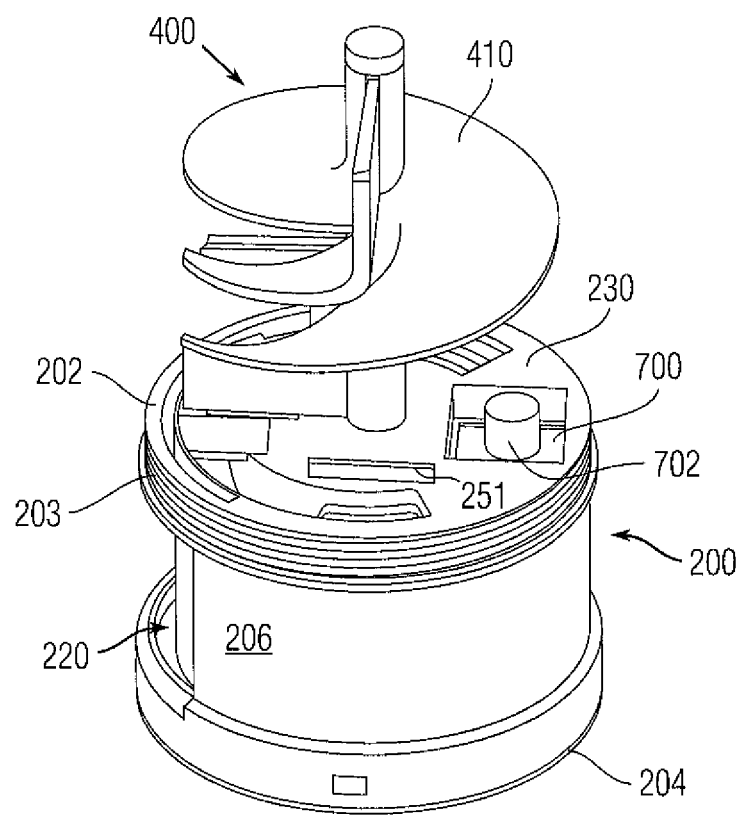
FIG. 3 is a top and side perspective view of bottom components of the pill dispenser device of FIG. 1 including the casing and pill dispensing mechanism shown without the pill bottle.
Figure 12:
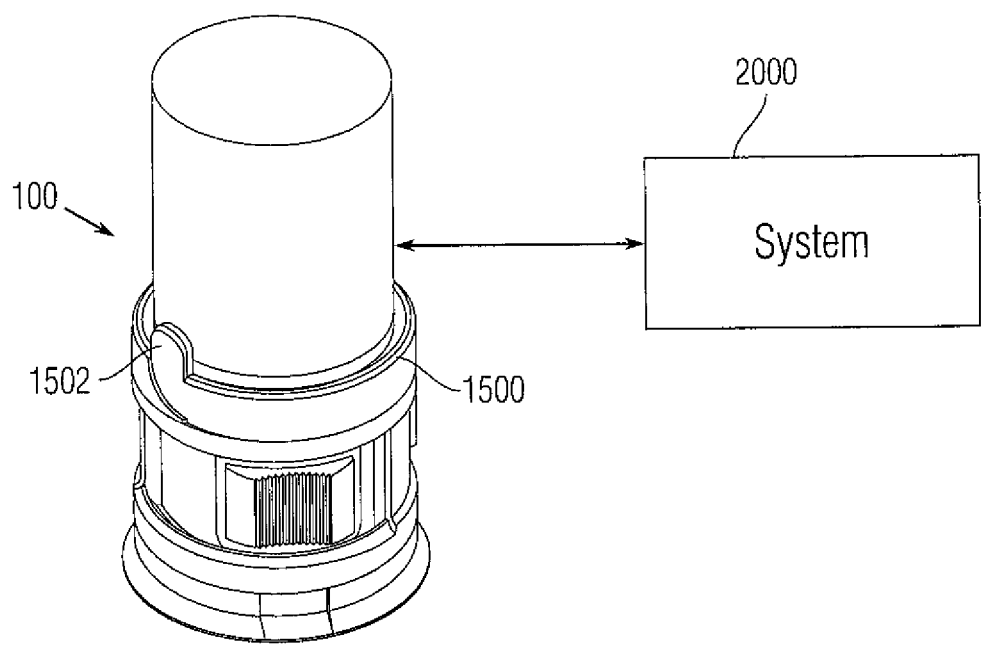
FIG. 12 shows the pill dispenser device as part of a communications network.
Figure 13:
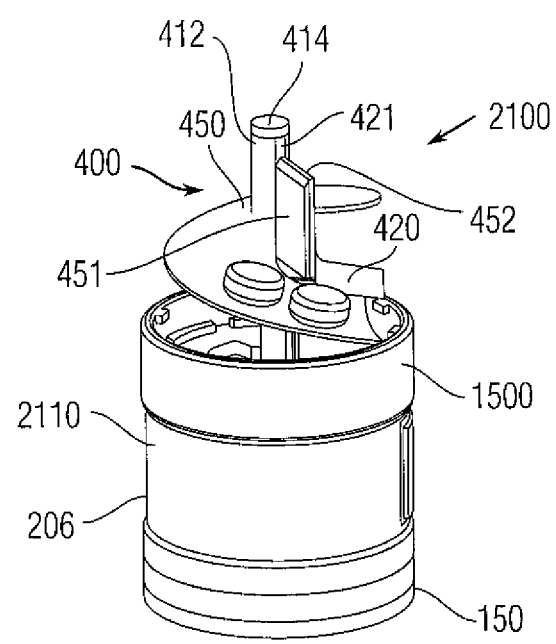
FIG. 13 is a top and side perspective view of a pill dispenser device according to another embodiment present invention with the pill bottle being removed for ease of illustration.
Figure 14:
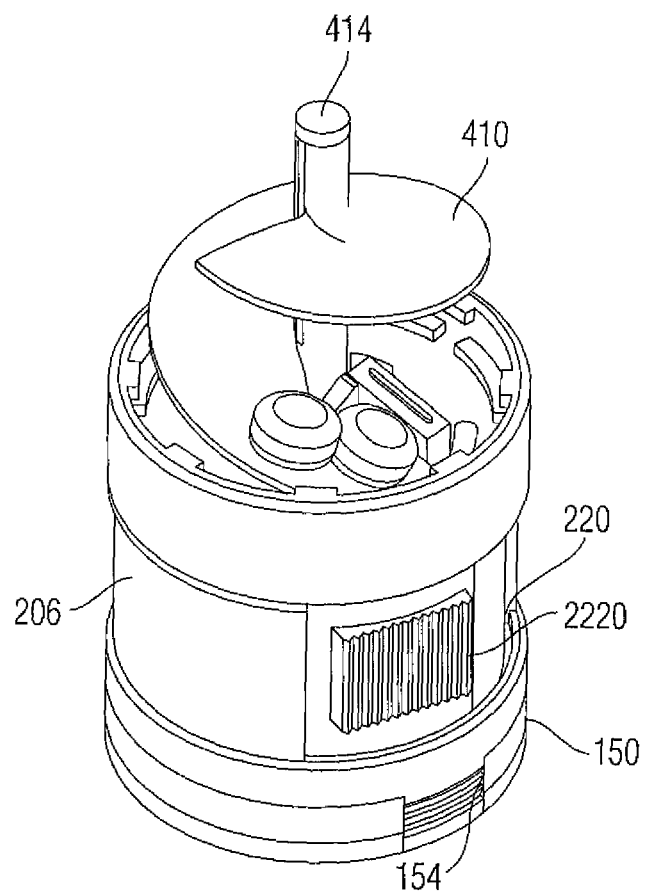
FIG. 14 is a top and side perspective view of bottom components of the pill dispenser device of FIG. 1 including a base, casing and pill dispensing mechanism shown without the pill bottle.
Figure 15:
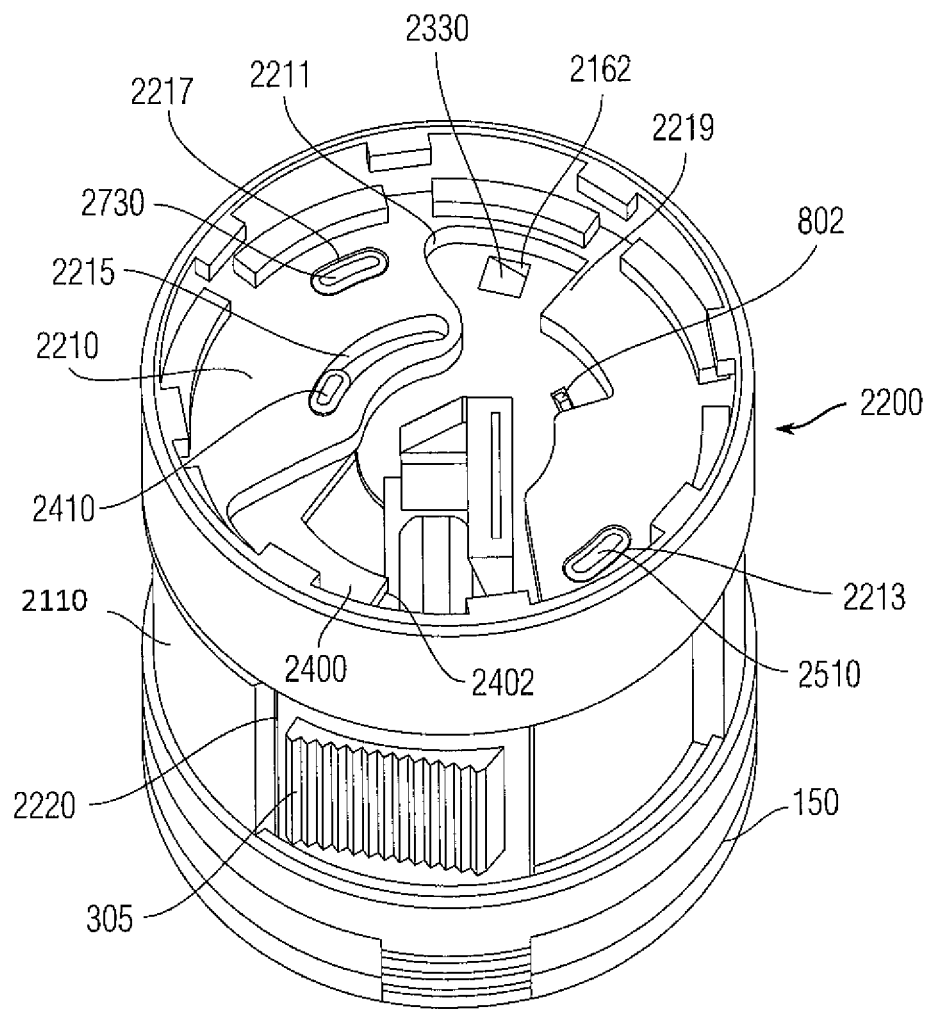
FIG. 15 is a top and side perspective view of the casing and pill door member in a closed position.
Figure 16:
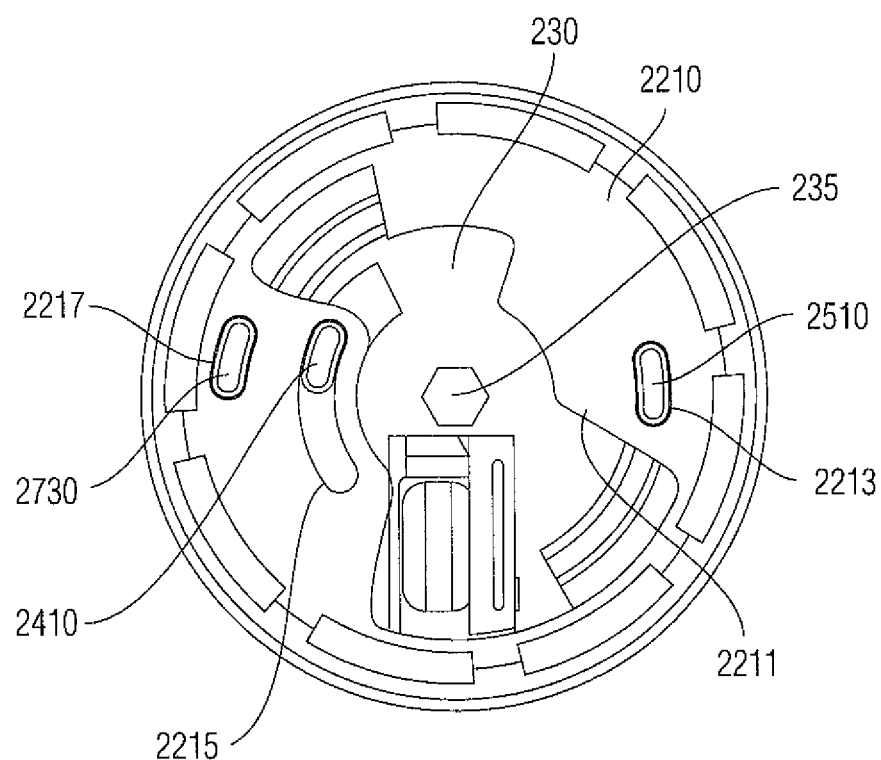
FIG. 16 is a top plan view of the assembled casing and pill door member.

FIG. 1 shows a medication dispensing device 100 according to the present invention that can be and is preferably part of a medication compliance system 2000 (FIG. 12). The medication dispensing device 100 is formed of a number of individual parts that when assembled form the medication dispensing device 100. In particular, the dispensing device 100 is in the form of a cap structure that is configured to mate with a conventional pill bottle 110. As discussed below, a secure and non-releasable connection is formed between the pill bottle 110 and the dispensing device 100 so as to prevent an individual, such as the patient or another, from tampering with and gaining access to the contents of the pill bottle 110. The pill bottle 110 is thus filled by an authorized person, such as a pharmacist, and then the dispensing device 100 is securely mated to the pill bottle 110 in the manner described below and is then ready for delivery to the patient, etc. A traditional pill bottle 110 is cylindrically shaped and includes a neck portion to which a traditional cap or in the present instance, the pill dispensing device 100, is securely attached. The size of the pill bottle 110 is dictated among other things by the size and shape of the pills and also the prescription regimen (e.g., how many pills are taken each day and length of the prescription).

Referring to FIGS. 1-13, the pill dispensing device 100 includes a base 150. The base 150 is constructed so that when the pill bottle 110 is inverted, the base 150 rests on a support surface, such as a table, and supports the pill bottle 110 in an upstanding position. In the illustrated embodiment, the base 150 has a circular shape and includes an inner face or surface 152 that faces the pill bottle 110. The base 150 has a beveled lower portion 151 and an upper portion 153 that is defined by an annular shaped wall with the inner surface 152 being a floor that is located generally at the interface between the portions 151, 153.

Along the circumference of the base 150, a notch or opening 154 is formed. In the illustrated embodiment, the notch 154 is generally square or rectangular shaped.

The pill dispensing device 100 also includes a casing or housing 200 which securely mates with the base 150. A secure mechanical attachment, such as a snap-fit type attachment, can be used to attach the casing 200 to the base 150. For example, the base 150 can include locking tabs that mate with locking openings or notches that are formed in the housing 200 so as to provide a secure snap-fit attachment. The illustrated casing 200 is a cylindrically shaped structure with a top end 202 and an opposing bottom end 204 that faces and mates with the base 150. Since the casing 200 is an at least partially hollow member, when the casing 200 is attached to the based 150, one or hollow interior spaces are formed and, as described herein, can contain and hold a number of components of the device 100 as described herein. The casing 200 is also defined by a side wall 206 that can be in the form of an upstanding circumferential wall.

The side wall 206 includes a recessed portion or track 220. In other words, the recessed portion 220 is set back relative to the other portions of the side wall 206 so as to define an arcuate shaped track that receives and limits the degree of lateral movement of another part as described below. Within the recessed portion 220 of the side wall 206, a medication (pill) dispensing opening (window) 215 (FIG. 3) is formed. The window 215 is open to the hollow interior of the casing 200.

The top end 202 is defined by a circumferential fastening feature 203, such as threads, that are formed along a circumferential band structure at the top end 202. At the top end 202, a top surface 230 is defined. The top surface 230 can be an at least substantially planar surface; however, it includes a number of features formed therein. More specifically, the top surface 230 includes a first opening or recess 235 that is generally centrally located. In the illustrated embodiment, the recess 235 is a hexagonal shaped recess; however, it will be appreciated that the recess 235 can have any number of other shapes that are designed to restrict movement of the object that is received therein (e.g., the recess 235 is a multi-sided recess that prevents free rotation of the object received therein). Proximate the recess 235, a shaped slot 231 is formed in the top surface 230. In the illustrated, the shaped slot 231 has a linear portion with a curved portion at one end. The curved end portion is closest to the recess 235. The recess 235 and slot 237 are not through holes and therefore, have floors.

The recessed portion or track 220 is recessed a sufficient distance such that a slot is formed between the recessed track 220 and the threads 203 that extend across the top edge of the recessed track 220.

The casing 200 includes a through opening 237 that is in registration with the notch 154 of the base 150 when the casing 200 and base 150 mate together. This registration permits an object to be passed from the underside of the base 150 through the casing 200. Unlike the notch 154 that is open along the side of the base 150, the through opening 237 is a completely bounded opening. For example, an arcuate wall section encloses the through opening 237 at the peripheral edge of the casing 200. The arcuate wall can include a fastening feature for attaching an object (described below) to the casing 200 after insertion through the notch 154.

The casing 200 also includes a number of recessed tracks formed therein along and within the top surface 230. More specifically, the top surface 230 includes a first recessed track 240 that is formed proximate a peripheral edge of the casing 200 and a second recessed track 250 that is formed proximate a peripheral edge of the casing 200. The through opening 237 is located between the recessed tracks 240, 250. Each of the first and second recessed tracks 240, 250 has an arcuate shape since the track runs along a length of the circumferential peripheral edge of the casing 200. The first recessed track 240 is a multi-layer recess in that a center portion 242 of the track 240 has a maximum depth and a recessed landing 244 is formed about the center portion 242. The landing 244 is recessed a first distance relative to the top surface 230 and a floor of the center portion 242 is recessed a second distance relative to the top surface, with the second distance being greater than the first distance. As shown in the figures, the center portion 242 does not extend the entire distance of the recessed track 240 and instead is formed at one end thereof.

Similarly, the second recessed track 250 is a multi-layer recess in that a center portion 252 of the track 250 has a maximum depth and a recessed landing 254 is formed about the center portion 252. The landing 254 is recessed a first distance relative to the top surface 230 and a floor of the center portion 252 is recessed a second distance relative to the top surface, with the second distance being greater than the first distance. As shown in the figures, the center portion 252 does not extend the entire distance of the recessed track 250 and instead is formed at one end thereof. Unlike the center portion 242, the center portion 252 extends a substantial length of the track 250.

The recessed center portions 242, 252 thus in themselves represent tracks having defined end points.

Figure 4:
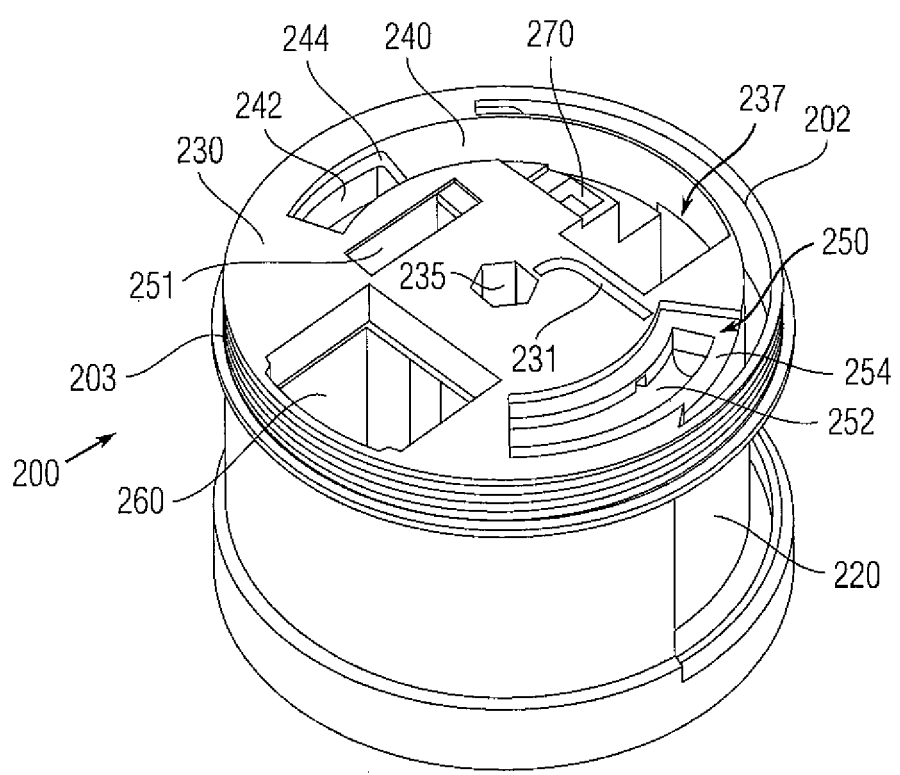
FIG. 4 is a top and side perspective view of the casing.
Figure 5:
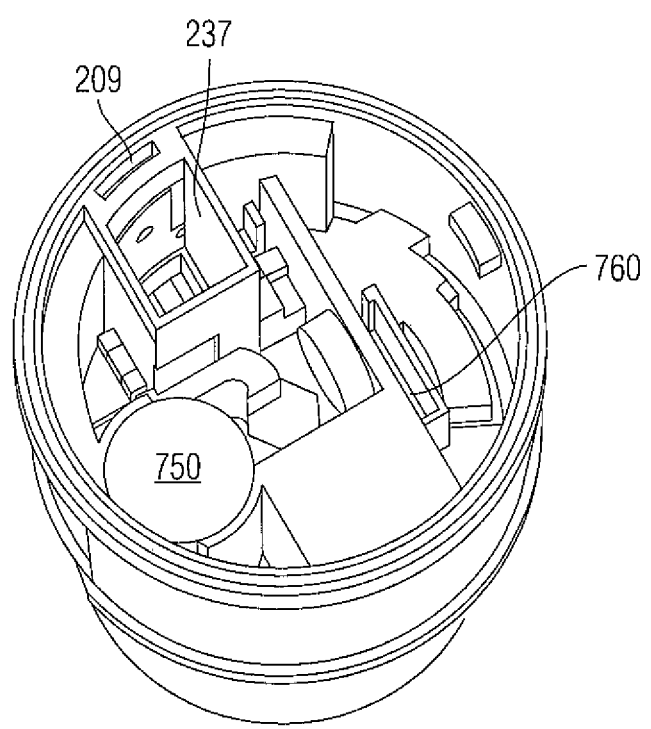
FIG. 5 is a bottom perspective view of the casing.
Figure 6:
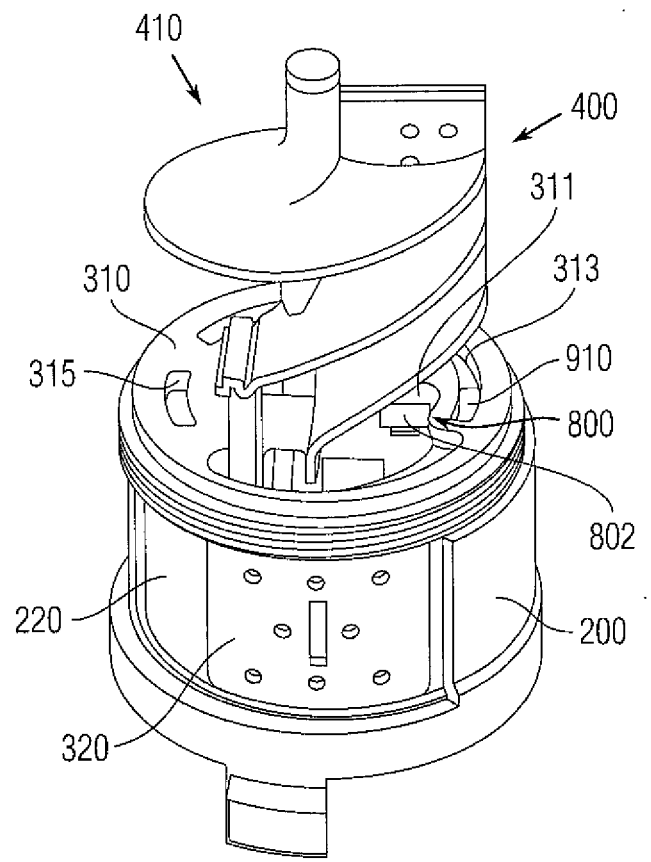
FIG. 6 is a front and side perspective view of the pill dispensing mechanism and the casing.
Figure 7:
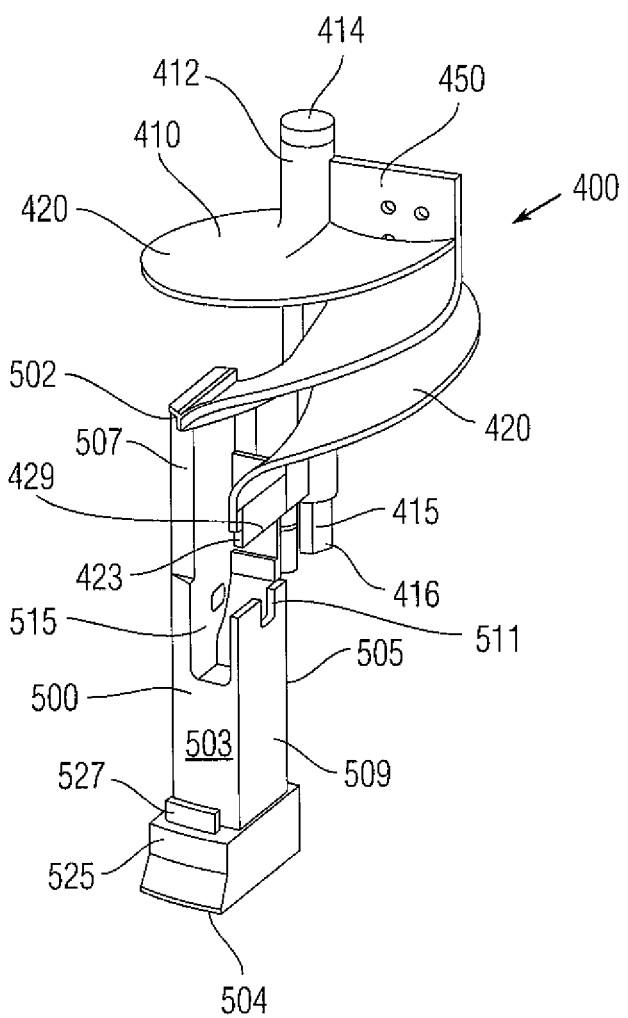
FIG. 7 is a side perspective view of the pill dispensing mechanism.

The length of the second recessed track 250 is less than the distance of the first recessed track 240. As shown in FIG. 4, the first and second recessed tracks 240, 250 are generally opposite one another. While the first recessed track 240 is open to the through opening 237, the second recessed track 250 is not open to the through opening 237 and terminates at a location spaced therefrom.

The casing 200 also includes a second through opening 251 that is formed therein and is open along the top surface 230. The second through opening 251 is located between the first recessed track 240 and the recess 235. The casing 200 also includes a recessed section 260 that is formed near the periphery of the casing 200. The recessed section 260 is located generally opposite the through opening 237. The recessed section 260 is not a through hole but instead includes a floor on which an object can be supported. In addition, another recessed portion 270 is formed adjacent the first recessed track 240 and adjacent the through opening 237. In the illustrated embodiment, the recessed portion 270 has a rectangular shape.

Between the assembled casing 200 and the base 150, a number of working components are contained within the hollow interior spaces. For example, a power source and electronic components of the device 100 can be stored and operatively connected to the working components of the device 100 as described below.

The device 100 also includes a movable (slidable) door member 300 that mates with the casing 200 and selectively allow opening of the window 215. The door member 300 includes a top portion 310 that seats against the top surface 230 of the casing 200 and a door portion 320 that extends downwardly form the top portion 310. As shown in the figures, the top portion 310 is in the form of an annular shaped disk-like structure and the door portion 320 is in the form of an arcuate shaped tab that is designed to travel within the recessed portion or track 220 and cover the window 215. The door portion 320 is formed at a right angle to the top portion 310 and thus represents a vertical portion, while the top portion 310 represents a horizontal portion.

The top portion 310 is substantially hollow and in particular, the top portion 310 includes a main through opening or slot 311 and a first arcuate shaped opening or slot 313 and a second arcuate shaped opening or slot 315, both of which are located proximate and extending along a length of the peripheral edge of the top portion 310. The slots 313, 315 are through openings. The first arcuate shaped slot 313 is intended for placement over the first recessed track 240 and the second arcuate shaped slot 315 is for placement over the second recessed track 240.

The disk-shaped top portion 310 has a complementary shape relative to the casing and therefore, can be a circular shaped disk that rests on the top surface 230 of the casing 200. The diameter of the disk-shaped top portion 310 is selected so as to not extend over the threads 203 at the top end 202. In addition, the door portion 320 is received within the opening (arcuate slot) formed between the recessed track 220 and the threads 203 that extend across the top edge of the recessed track 220. In this manner, the disk-shaped top portion 310 can seat against and be supported by the top surface 230 while the door portion 320 is disposed within the recessed track 220 in such a way that the disk-shaped top portion 310 can freely rotate on the top surface 230 and the door portion 320 can slidingly travel within the recessed track 220.

A thumb grip member 305 is attached to the door portion 320 to provide a rough surface that is configured to receive a thumb or finger of the patient or individual for laterally sliding the door portion 320 within the recessed track 220. The thumb grip member 305 attaches to the door portion 320 using traditional techniques, such as a mechanical attachment, e.g., a snap fit.

The recessed track 220 has a medication loading position at one end and medication release position at the opposite end with the center position being idle. The door portion 320 is sized and designed to cover the pill dispensing window 215 except for when the door member 300 is permitted to move into the medication release position as described herein. In the medication loading position, the door portion 320 is disposed over the medication dispensing window 215 and therefore, the medication is prevented from being dispensed. Conversely, when the door portion 320 is in the medication release position, the door portion 320 is offset from the medication dispensing window 215 and therefore, the medication is free to be dispensed as described herein.

The degree of travel of the door portion 320 within the recessed track 220 is limited and defined by the end walls/edges of the recessed track 220. In other words, when the door portion 320 abuts one end wall of the recessed track 220, the door portion 320 has reached one end of travel and when the door portion 320 abuts the other end wall of the recessed track 220, the door portion 320 has reached the other end of travel.

The device 100 also includes a pill track and dispenser assembly 400 that is at least partially selected in view of the type of pill that is contained in the pill bottle. The pill track and dispenser assembly 400 includes two main parts, namely, a pill track member 410 and an insert 500 that mates with the pill track 410 and configures the pill track 410 to have a desired orientation that allows the pills to only travel in a desired, predetermined orientation relative to the pill track 410. The predetermined orientation can be a horizontal orientation, vertical orientation, or even a diagonal orientation, etc. In one embodiment, the pill track 410 is constructed to cause the pills to lie horizontal as opposed to lying vertically (i.e., on their sides); however, in other embodiments, the pills can lie in other orientations, such as being oriented vertically as the pills travel down the slot and into the dispensing window.

The pill track 410 includes a central shaft 412 that has a first end 414 and an opposite second end 416, with the first end 414 representing the top end of the shaft 412. The central shaft 412 is a hollow cylindrical rod like structure that is not completely closed along its complete circumference. Instead, a vertical slot 421 is formed within the central shaft 412 that opens to the hollow interior and extends along a length of the central shaft 412.

The pill track 410 includes two ramp-like structures that control movement of the pills as they travel from the pill bottle to a dispensing location as described below. More specifically, the pill track 410 includes a fixed ramp part 420 that has a helical shape and a movable ramp that is in the form of a movable pill height adjuster member 450 that is disposed between portions of the fixed ramp part 420 and is movable so as to adjust the pill track height along at least a portion of the fixed ramp part 420. The fixed ramp part 420 is fixedly attached to the central shaft 412 and wraps therearound due to the helical shape of the ramp part 420.

The movable pill height adjuster member 450 also has a generally helical shape with a top edge 452 and a bottom edge 455. The top edge 452 is part of a generally vertical wall and the bottom edge 455 includes a fastening feature 458 that is configured to mate with and provide a secure connection between the member 450 and the insert 500. For example, the fastening feature 458 can provide a mechanical attachment between the two parts and in particular, the fastening feature 458 can be configured to provide a snap-fit between the member 450 and the insert 500. In the illustrated embodiment, the fastening feature 458 can be a female part (e.g., a U-shaped slot).

As shown in the figures, the helical shaped body of the member 450 is intended to complement and mirror to a degree the helical shape of the portion of the fixed ramp part 420 that lies below the member 450. It will be appreciated that as a pill travels down the top portion of the fixed ramp part 420, the pill encounters the member 450 and in particular, the member 450 and underlying fixed ramp part 420 define a space that is formed therebetween for receiving the pill only if the pill is within the desired orientation (e.g., horizontal, vertical or diagonal). The member 450 can thus be thought of as defining a ceiling and the underlying fixed ramp part 420 represents a floor. If the pill is in an undesired upstanding position (i.e., standing vertically about its side when the desired orientation of the pill is horizontal along the pill track), the pill is unable to fit within the space between the member 450 and the fixed ramp part 420 and therefore, will not travel further downward toward the pill dispensing location. However, the member 450 is designed to correct the mis-orientation of the pill but causing an upstanding pill to change its orientation and fall into a horizontal position along the fixed ramp part 420, and thereby, can travel further along the fixed ramp part 420 to the pill dispensing location. In other words, the distance between the member 450 and the fixed ramp part 420 is selected so that pills can only be received therebetween if they are in the horizontal position (lying flat). However, as discussed herein, it will be appreciated that other pill orientations are possible, such as the pill lying vertically or diagonally.

The bottom end 429 of the fixed ramp 420 includes a coupling edge 423 that is received within the shaped slot 237 formed in the top surface 230, thereby securely anchoring the fixed ramp 420 to the top surface 230 of the casing 200.

At the second end 416, the central shaft 412 includes a coupling section 415. In particular, the coupling section 415 has a shape different than the rest of the length of the central shaft 412. The coupling section 415 is configured to seat within the recess 235 that is formed in the top surface 230. In the illustrated embodiment, the coupling section 415 has a hexagonal shape that is received within the complementary hexagonal shaped recess 235. A frictional fit is formed between the coupling section 415 and the top surface 230 resulting in the pill track member 410 standing upright.

The member 450 includes a tab portion 451 that is received within the hollow interior of the central shaft 412 and extends through the vertical slot 421. By disposing the tab portion 451 within the interior of the central shaft 412 by passing through the vertical slot 421, the member 450 is limited to vertical movement along the height of the central shaft 412. The vertical slot 421 is formed along the central shaft 412 in a region between the helical ramp portions of the fixed ramp 420 so as not to interfere with the formation of the fixed ramp 420.

The member 450 is biased within the interior of the central shaft 412 and more specifically, a biasing member (not shown) is disposed within the hollow interior of the central shaft 412. The biasing member, such as a spring, has a first end that mates with an end cap 415 that is disposed at the first end 414 so as to close off the open end of the hollow central shaft 412 and a second end that mates with the tab portion 451. The biasing member 459 is constructed so that it applies a biasing force against the member 450 so as to position the member 450 in a down position. The down position is thus the rest position of the member 450. In the down position, the member 450 is disposed closest to the underlying portion of the fixed ramp 420. In other words, in the down position, the space between the ramp shaped body of the member 450 and the underlying ramp portion of the fixed ramp 420 is at a minimum (relative to the permitted degree of travel). This distance is set at a minimum for smaller sized pills.

As described herein, the construction of the insert 500 dictates the position of the movable member 450. In particular, since the member 450 is coupled directly to the insert 500, the insertion of the insert 500 into the casing 200 and the height of the insert 500 results in the movable member 450 being positioned along the central shaft 412. As described herein, the insert 500 can apply an upward force to the member 450, thereby causing upward movement of the member 450 within the central shaft 412 by compression of the biasing member within the central shaft 412. It will be appreciated that as the movable member 450 rides upward within the central shaft 412, the distance between the member 450 and the underlying ramp portion of the fixed ramp 420 increases so as to accommodate larger sized pills. The movable member 450 thus travels between the ramp portions of the helical shaped fixed part 420.

As described in greater detail hereinbelow, the movable member 450 provides a means for adjusting the characteristics of the pill dispensing ramp so as to ensure that the pills are properly oriented as they are delivered to the pill dispensing location. For example, the pills ride down the ramp in a horizontal position as opposed to an upstanding vertical position. The movable member 450 is thus a spring biased member that controls pill orientation as the pills travel down the pill track.

The insert 500 is an elongated structure that has a first end 502 and an opposite second end 504, with the first end 502 representing the top and the second end 504 representing the bottom. The insert 500 also includes a front surface 503 and a rear surface 505, as well as a first side wall 507 and a second side wall 509. In the illustrated embodiment, the insert 500 generally has, in part, a block-like appearance.

The insert 500 is shaped and sized to be received within both the notch 154 and the through opening 237 that is in registration with the notch 154 of the base 150 when the casing 200 and base 150 mate together. The insert 500 has a hollow center space with the first side wall 507 having a height that is greater than the height of the second side wall 509. In particular, the second side wall 509 extends about half the height of the first side wall 507 and therefore, the insert 500 has a lower portion 510 that is defined between the first side wall 507 and the second side wall 509.

The pill track 400 is attached to the insert 500 at the first end 502 of the insert 500. As mentioned above, the bottom edge 455 of the movable member 450 includes a fastening feature 458 and the first end 502 include a complementary fastening feature that mates therewith to provide a secure connection between the two parts. For example, the fastening feature at the first end 502 can be a male/female member and in the illustrated embodiment, the fastening feature is a male projection that is received into the U-shaped slot of the fastening feature 458, thereby forming a mechanical attachment (e.g., friction fit) between the parts. The movable member 450 is thus coupled to both the central shaft 412 and the insert 500 in such as way that vertical movement thereof is permitted.

The lower portion 510 that is defined between the first side wall 507 and the second side wall 509 includes a U-shaped slot 515 that is defined between the side walls 507, 509 and a rear wall 511. The U-shaped slot 515 is thus open along the front of the insert 500 and as described herein is in registration with the window 215 formed in the side wall of the casing 200. The U-shaped slot 515 is thus part of the pill dispensing exit. The curvature of the movable member 450 and the fixed ramp 420 directs pills toward the U-shaped slot 515. As shown, pills travel down the helical shaped fixed ramp 420 and drop into the U-shaped slot 515. As described herein, while a plurality of pills can be disposed within the vertical U-shaped slot 515, only a single pill is dispensed at one time. The curved nature of the ramp 420 and the location and orientation of the U-shaped slot 515 cause the pills to slide down the ramp 420 while lying on their bottom (or top) surfaces, the pills assume a vertical orientation as they drop into the U-shaped slot 515 (i.e., they lie on their sides in stacked orientation). The U-shaped slot 515 is sized and shaped so that the pills cannot change their positions after entering the U-shaped slot 515 from the ramp 420. In other words, the pills cannot assume a more horizontal shape.

The second side wall 509 includes a notch or opening 511 that is open along the top edge thereof.

The insert 500 includes a base portion 525 at its bottom end that is intended to securely attach to the casing 200 and also to close off the notch 154 of the base 150. The base portion 525 includes a fastening element 527 that in the illustrated embodiment is in the form of a projection (male feature) that is received within the complementary opening 209 (FIG. 5) of the casing 200. For example, a mechanical attachment (i.e., friction fit) can be formed between the base portion 525 and the casing 200. The base portion 525 thus has an arcuate peripheral edge that generally completes the circumference of the base 150. The attachment between the insert 500 and the base 150 can be of a type which prevents or makes it very difficult to remove the insert 500 from the device 100.

The insert 500 is introduced into the hollow interior of the casing 200 by being passed through the notch 154 and the through opening 237 and then into contact with the movable member 450. In other words, the fixed ramp structure 320 is oriented so as to not interfere with the reception of the insert 500 into the hollow interior of the device 100. The first end 502 of the insert 500 does come into contact with the fastening feature 458 so as to provide a secure attachment.

It will be appreciated that the height of the insert 500 directly controls the positioning of the pill adjusting track member 450 due to the coupling therebetween. Thus, if the insert 500 has a greater height, the member 450 is pushed further upward (against the force of the biasing force), thereby creating a larger space between the underside of the member 450 and the underlying ramp 420 to accommodate larger sized pills.

As shown in the figures, the insert 500 passes through the main slot 311 formed in the top portion 310 of the door member 300. The insert 500 is stationary; however, the shape of the main slot 311 is configured to permit a degree of rotation of the top portion 310 above the casing 200 before interference between the door member 300 and the insert 500.

The device 100 also includes a controllable pill release mechanism 600. The pill release mechanism 600 includes both mechanical and electronic features and in particular, the pill release mechanism 600 includes an actuator 700 (FIG. 3) that permits controlled movement of the door member 300 relative to the casing 200 so as to open the drug dispensing window (opening) under select conditions to allow dispensing of a pill. The electronic components further include a power source 750 (FIG. 5) that can be in the form of a battery that is stored within the hollow interior of the casing 200 and a processor 760 (FIG. 5), such as a printed circuit board, that is electrically connected to the power source 750 and the actuator 700 for powering and controlling operation of the actuator 700.

The actuator 700 can be in the form of a solenoid that has a movable pin/projection 702 that is vertically oriented. The actuator 700 is arranged in an upstanding member with the pin 702 being located at the top of the actuator 700 such that the pin 702 moves vertically between an extended position and a retracted position. The actuator 700 is disposed within the recessed section 260 of a casing 200.

The actuator 700 is positioned such that the top portion 310 of the door member 300 is disposed above the actuator 700. However, when the pin 702 is the extended position, the pin 702 assumes a position higher than the top surface of the top portion 310 when the pin 702 is received within the main opening 311 formed in the top portion 310. As described herein, when the pin 702 is received within the main opening 311 when the pin 702 is in the extended position. As described herein, this extended position of the pin 702 prevents free rotation of the door member 310 relative to the casing 200.

The device 100 also includes a switch 800 that is disposed within the second through opening 251 and therefore is open and in communication with the door member 300 is select positions of the top portion 310. The switch 800 can be in the form of a rocker switch that includes a pivotable portion 802 (FIG. 6. The pivotable portion faces the top portion 310 and movement of the top portion 310 over the casing 200 causes the switch 800 to move between open and closed positions. In particular, when the main opening 311 of the top portion 310 lies above the rocket switch 800, the pivotable portion thereof is free to assume the open position since the top portion 310 does not provide interference. As the door member 300 is operated, as described below for loading and dispensing the medication, the top portion 310 is rotated into contact with the pivotable portion 802 of the switch 800 and causes a closing thereof. When the pivotable portion 802 is compressed and the switch assumes a closed position, the switch 800 sends a control signal to the processor 760.

The controllable pill release mechanism 600 also includes a plunger member 900 that is designed to control the loading and dispensing of the pills through the pill dispensing window 215. The plunger member 900 is an arcuate shaped member that is disposed and has a degree of travel within the first recessed track 240. The plunger member 900 has a first end 902 and an opposing second end 904. The plunger member 900 also includes a top surface 905 that includes protrusion or tab 910 extending upwardly from the top surface 905. The plunger member 900 also includes a bottom portion that is received within the center portion 242, while the remaining portion is disposed on the landing 244. The arcuate shape of the plunger member 900 is complementary to the arcuate shape of the first recessed track 240 and therefore can move therein. The second end 904 can be a flat end.

The plunger member 900 is thus coupled to the casing 200 by having a portion captured within the center portion 242 and within the first recessed channel 240 and to the top portion 310 of the door member 300 as a result of the tab 910 being received within the first arcuate shaped slot 313 of the top portion 310. The plunger member 900 is biased such that it normally assumes a closed position in which the second end 904 of the plunger member 900 extends into the U-shaped slot 515 into either contact with one pill or against the first side wall (whereby the plunger member 900 extends completely across the U-shaped slot 515) due to the first recessed channel 240 being freely open to the insert 500. The plunger member 900 is biased using a biasing member, such as a spring that can be captured within the center portion 242. The biasing member thus biases the plunger member 900 to the closed position in that the plunger member 900 is driven toward the insert 500 and into the U-shaped 515 for controlling movement of the pills.

Besides the tab 910, the plunger member 900 is disposed below the top portion 310 of the door member 300. The plunger member 900 is thus a passive member that is captured by the door member 300 by means of the tab 910 being contained in the slot 313 and therefore, rotation of the door member 300 causes movement of the plunger member 900 within the first recessed channel 240. When the door member 300 is moved counterclockwise, the movement of the door member 300 causes the tab 910 to move counterclockwise, thereby causing the biasing member (to store energy). When the user releases the door member 300, the biasing member releases its energy and the plunger member 900 is driven towards the insert 500.

The controllable pill release mechanism 600 also includes a door return member 1000. The door return member 1000 has an arcuate shape member that is disposed and has a degree of travel within the second recessed track 250. The door return member 1000 has a first end and an opposing second end. The door return member 1000 also includes a top surface 1005 that includes protrusion or tab 1010 extending upwardly from the top surface 1005. The door return member 1000 also includes a bottom portion that is received within the center portion 252, while the remaining portion is disposed on the landing 254. The arcuate shape of the door return member 1000 is complementary to the arcuate shape of the second recessed track 250 and therefore can move therein.

The door return member 1000 is thus coupled to the casing 200 by having a portion captured within the center portion 252 and within the rest of the second recessed channel 250 and to the top portion 310 of the door member 300 as a result of the tab 1010 being received within the second arcuate shaped slot 315 of the top portion 310. The door return member 1000 is biased such that it normally assumes a closed position in which the door portion 320 closes the pill dispensing window 215. The door return member 1000 is biased using a biasing member, such as a spring, that can be captured within the center portion 252. The biasing member thus biases the door return member 1000 to the closed position in that the door return member 1000 is positioned such that the door portion 320 closes the window 215 by being disposed in front of the window 215 (i.e., door member 300 is in the idle position).

Besides the tab 1010, the door return member 1000 is disposed below the top portion 310 of the door member 300. The door return member 1000 is thus a passive member that is captured by the door member 300 by means of the tab 1010 being contained in the slot 315 and therefore, rotation of the door member 300 causes movement of the plunger member 900 within the second recessed channel 250. When the door member 300 is moved clockwise, the movement of the door member 300 causes the tab 1010 to move clockwise, thereby causing the biasing member (to store energy). When the user releases the door member 300, the biasing member releases its energy and the door return member 1000 is driven towards the insert 500, thereby causing the door portion 320 to close.

Thus, the two biasing members associated with the plunger member and the door return member operate on the door member 300 to position the door portion 320 in a rest position in which it covers the pill dispensing window 215 formed in the casing side wall. As explained below, the door member 300 can be moved to at least two other positions and in particular, the door member 300 can be placed in a drug (pill) dispensing position by rotating the door member 300 clockwise, as described below, or can be placed in a drug (pill) load position by rotating the door member 300 counterclockwise.

The device 100 includes an emergency tab 1500 that mates with and is fixedly attached to top end 202 of the casing 200. For example, the emergency tab 1500 can be attached using the fastening feature 203. The emergency tab 1500 is preferably fixedly attached to the casing 200 in a tamper proof manner in that if there is an attempt to remove the emergency tab 1500, it will be readily apparent by looking at the device 100. This prevents the patient from gaining unauthorized access to the pills in the pill bottle 110. The emergency tab 1500 is also directly coupled to the open end of the pill bottle 110 in a tamper proof manner in that the patient is prevented from removing the pill bottle 110 from the emergency tab 1500 without visibly modifying/damaging the emergency tab 1500. For example, a mechanical attachment, in the form of a snap-fit, can be provided between the pill bottle 110 and the emergency tab 1500. The snap-fit is of a type that cannot be disengaged by the patient and thus, once the filled pill bottle 110 is snap-fittingly mated with the emergency tab 1500, the two parts cannot be separated.

As such, the emergency tab 1500 is designed to prevent authorized access to the medication contained within the pill bottle 110. As shown, the emergency tab 1500 includes an accessible tab 1502 that can be grasped by the patient in an emergency situation where the contents of the pill bottle 110 need to be accessed. For example, since the device 100 controls the dispensing of the pills so as to strictly follow the prescribed prescription regimen, pills cannot be accessed at unauthorized times that fall outside a medication prescription window. Thus, if the patient accidently loses the medication as by dropping it down the drain, etc., and the patient urgently needs to access the medication, the patient may have no choice but to break the seal between the bottle 110 and the device 100 as by pulling the pull tab 1502 of the emergency tab 1500. However, when the patient returns to consultation with the physician and/or seeks refill, it will be immediately apparent that the emergency tab 1500 has been removed and this will spur questions and require explanation.

The tab 1502 can be connected to the rest of the emergency tab 1500 with a score line and therefore, the tab 1502 can represent a pull tab that when pulled by the patient 1500 causes the tab 1502 to unwind and separate from the casing 200 and the pill bottle 110. The pull tab 1502 is similar to those used in the beverage industry, such as by orange juice manufacturers.

The processor can also be configured to sense when the emergency tab 1500 has been ruptured. For example, the emergency tab 1500 can be in contact with a simple sensor (contact sensor) that is in electronic communication with the processor, that when the emergency tab 1500 is removed, a signal is generated and delivered to the processor. The processor can then record the date and time of the removal of the emergency tab 1500.

The device 100 also includes a pill sensor 1300 (FIG. 8) that is in electronic communication with the processor. The pill sensor 1300 senses the presence of a pill within the U-shaped slot 515 of the insert 500. The pill sensor 1300 can be associated with and supported by the casing 200 and seats within the notch 511 that is formed in the second side wall 509 of the insert 500. The pill sensor 1300 can therefore at least partially extend into the U-shaped slot 515; however, in any event, the pill sensor 1300 is configured to detect the presence of a pill within the U-shaped slot 515. Any number of different sensors can be used for the pill sensor 1300 so long as they perform the intended function. In one embodiment, the pill sensor 1300 is a photocell that detects the presence of the solid pill within the U-shaped slot 515. When the photocell 1300 detects a solid object (i.e., the pill), a signal is sent to the processor.

The mechanical operation of the device 100 is now described. Prior to the device 100 being delivered to the patient, the pill bottle 110 is filled with pills in view of the prescription order of the patient. Depending upon the prescription and in particular, the size and shape of the pills, the insert 500 is selected. As mentioned herein, the construction of the insert 500 including the height of the insert 500 and the shape and size of the U-shaped slot 515 are selected in view of the size of the pills. As discussed herein, the insert 500 controls the height of the movable member 450 and thus controls the pill track dimensions so as to cause the pills to ride along the helical-shaped ramp 420 in the desired position (i.e., on their bottom as opposed to their side).

After being properly selected, the insert 500 is inserted into the notch 154 of the base 150 and through the through opening 237 and through the main opening 311 of the top portion 310. The insert 500 is then attached to the movable member 450 as described herein and the base 150 is attached to the casing 200 as described herein.

The filled pill bottle 110 is then mated to the assembled device 100 by mating the open end of the pill bottle 110 with the device 100, such as by mating the open end of the pill bottle 110 with the emergency tab 1500 (e.g., in a non-releasable manner). The top end 414 of the pill track 410 is thus disposed within the loose pills contained in the pill bottle. Thus, some of the loose pills land on the pill track 410 and travel down the helical shaped ramp 420 when the bottle is inverted.

In the normal rest position of the device 100 (see FIG. 8), the door portion 320 of the door member 300 is disposed across the pill dispensing window 215 and thus a pill cannot exit therethrough. As will be appreciated, the pill dispensing window 215 is in select communication with the pill track 410 and the interior of the pill bottle 110 depending upon the position (location of the plunger member 900). The door portion 320 is generally centrally located within the recessed track 220 of the casing 200.

In this normal rest position, the plunger member 900, under the action of the biasing member, is in a closed position, in that the plunger member 900 is disposed at least partially within the U-shaped slot 515 and therefore, the pills are prevented from traveling to the bottom of the U-shaped slot 515 and to the window 215. Similarly, the door return member 1000, under the action of the biasing member, applies a force to the door member 300 to position it in the normal rest position.

Figure 11:
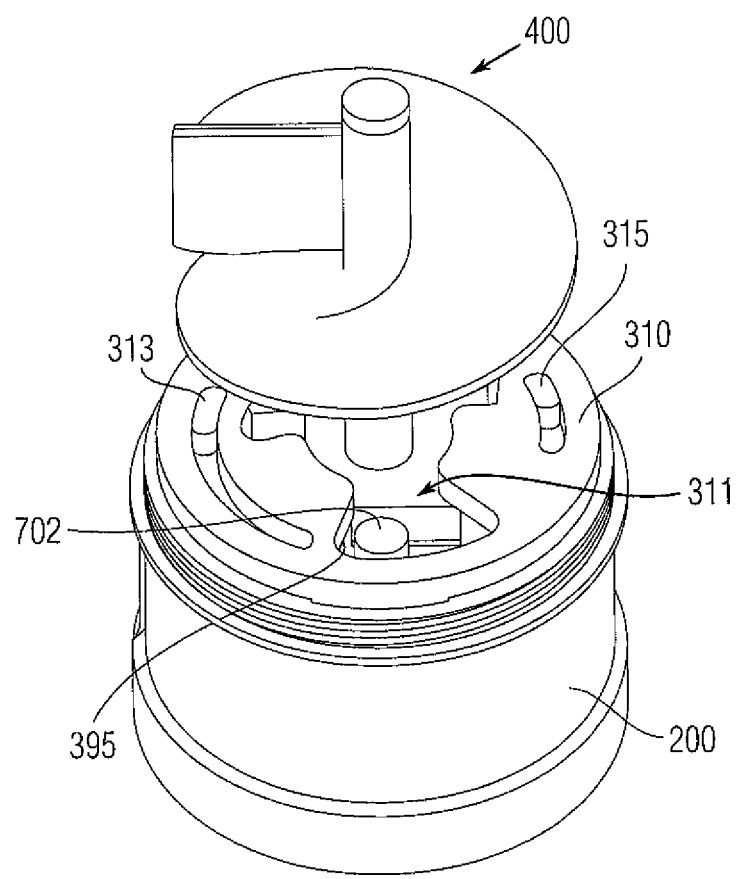
FIG. 11 is top and side perspective view of the device with the pill bottle removed.

In the normal rest position, the actuator 700 (e.g., solenoid) is in a position in which the movable pin/projection 702 is in an up (extended) position, the pin 702 assumes a position higher than the top surface of the top portion 310. The pin 702 prevents free rotation in both directions of the door member 310 relative to the casing 200. In particular, the pin 702 is disposed within a shaped end portion 395 of the main opening 311. As shown in FIG. 11, the shape of the end portion 395 defines the degree of travel of the door member 300 when the pin 702 is in the extended position. In other words, the two side edges of the shaped end portion are stops that prevent continued clockwise and counterclockwise movement of the door member 300 when the pin 702 is extended.

In the normal rest position, the extended position of the pin 702 of the solenoid (actuator) prevents the door member 300 from being moved into a position in which the pill dispensing window 215 is open. Thus, pills cannot be dispensed.

To load a pill into the U-shaped slot 315 of the insert 300, the door member 300 is moved within the recessed track 220 to a load position which is defined at one end of the recessed track 220. The user places his or her thumb or finger on the thumb grip member 305 and moves the door portion 320 within the recessed track 220 toward the load position. This movement is a counterclockwise movement of the door member 300.

Figure 10:
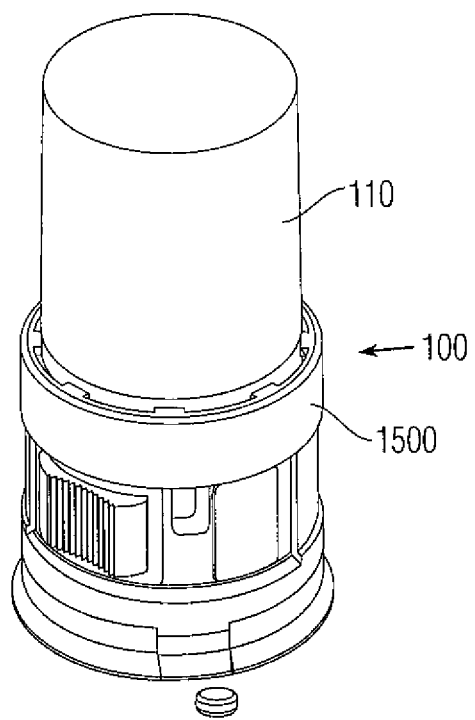
FIG. 10 is top and side perspective view of the device with a pill dispensed.

It will be appreciated that the door member 300 can be moved to the load position when the pin 702 of the solenoid 700 is in the extended position since the degree of travel provided by the shaped end portion 395 of the slot 311 permits such movement. This movement of the door member 300 to the load position also does not actuate the switch 800 since the main opening 311 of the top portion 310 remains over the switch 800 as the door member 300 moves into the load position. As the door member 300 moves counterclockwise, the upstanding tab 910 of the plunger member 900 is carried by the rotating door member 300 due to one end of the slot 313 engaging the tab 910 and thus, the further rotation of the door member 300 causes the tab 910 to move in a counterclockwise direction. The counterclockwise movement of the tab 910 causes the entire plunger member 900 to move in a counterclockwise direction within the recessed channel 240 and the biasing member to store energy. It will be appreciated that as shown in FIG. 10, this movement of the plunger member 900 in a direction away from insert 500 causes the U-shaped slot 315 of the insert 300 to become open to the bottom portion of the fixed ramp 420 and therefore, pills that are riding along the fixed ramp 420 can fall into place within the U-shaped slot 315 of the insert 300. As mentioned herein, the pills are loaded within the U-shaped slot 315 by being stacked in a vertical orientation with the pills seated on their sides. The bottommost pill seats against the floor (bottom surface) of the U-shaped slot 315.

However, in the load position, the door portion 320 of the door member 300 still remains in front of the pill dispensing window 215 and therefore, pills are prevented from being dispensed through the window 215 to the patient.

It will be understood that the motion of moving the door member 300 from the normal rest position to the pill load position causes the plunger member 900 to be retracted from the U-shaped slot 315 and therefore, pills can travel into the U-shaped slot 315. However, the dispensing window 215 remains closed and thus, no pills can be dispensed.

The patient can move the door member 300 to the load at any time including right after a pill has been dispensed but well before the next scheduled pill release as dictated by the prescription.

Figure 8:
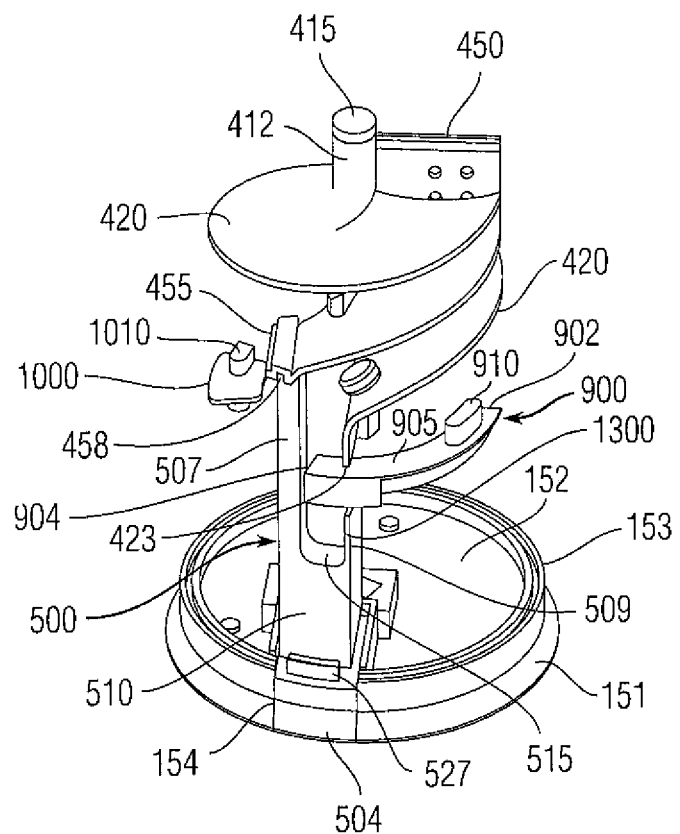
FIG. 8 is side perspective view of the pill dispensing mechanism and a base showing a plunger member in one position.

Once the user releases the thumb grip member 305 is released, the biasing member associated with the plunger member 900 applies a return force to the plunger member 900 which drives the plunger member 900 in a clockwise direction within the recessed channel 240 until the second end 904 of the plunger member 900 is within the U-shaped slot 315 (FIG. 8). As shown in the figures, the height of the U-shaped slot 315 and the position of the plunger member 900 are purposely chosen so that only one pill lies below the plunger member 900 when it is disposed within the U-shaped slot 315. This one pill that lies below the plunger member 900 is the one pill that is free to be dispensed as soon as the door member 300 is moved to the dispensing position and the window 215 is opened. The second end 904 of the plunger member 900 can thus be in contact and apply a force (generated by the biasing member) against the pill that lies immediately above the bottommost pill that is ready for dispensing as shown in FIG. 8. The biasing force applied by the plunger member 900 effectively pinches the next to dispense pill between the plunger member 900 and the first side wall 507 of the insert 500 and prevents its dispensing even when the door member 300 is moved to the dispensing position as described below.

When it is an appropriate time for a pill to be dispensed (as described in detail below), the user dispenses a pre-loaded pill by moving the door member 300 toward the dispensing position thereof. As the door member 300 is rotated clockwise and top portion 310 of the door member 300 comes into contact with and rides over the pivotable portion of the switch 800. When this occurs, a signal is sent to the processor and the processor performs an inquiry to determine whether the device 100 should be unlocked and permit dispensing of the medication by allowing the door member 300 to rotate clockwise a sufficient degree that results in the door portion 320 being offset from the window 215. The rocker switch 800 thus activates the solenoid 700 to allow the release of the pill.

The software component of the present invention is described below; however, in general, the inquiry can be based on a number (e.g., two or three) items of interest and the door member 300 is only permitted to move to the dispensing position if all of the inquiry items are satisfied. For illustration only, a system is described in which three inquiries have to be satisfied in order for the door member to move to the dispensing position; however, it will be appreciated that the software can be configured to allow the door member to move to the dispensing position when less than three inquiries are satisfied.

The first inquiry step performed by the processor is to determine whether it is time for a pill to be dispensed. It will be appreciated that the medication dispensing time periods are dictated by the patient's individual prescription regimen as set forth below. The second inquiry step performed by the processor is to determine whether there are still pills left for dispensing. For example, the processor will determine whether there is still a future pill dispensing event and thus, a need for dispensing of the pill. This inquiry is thus more than determining whether there are pills left in the pill bottle 110. The third inquiry step performed by the processor is to determine whether the sensor 1500 detects a pill in the pre-loaded position within the U-shaped slot 315. As mentioned above, the sensor 1500 detects the presence of a solid object (i.e., the pill) within a line of sight thereof.

If all three inquiries are satisfied, it is an appropriate time for dispensing of the pill and the door member 300 is permitted to move to the open, dispensing position as a result of the processor sending a signal to the actuator 700 (solenoid). This control signal causes the solenoid 700 to retract the pin 702 and the door member 300 is free to move to the dispensing position (i.e., the door member 300 is free to move to another end of the recessed track 220. The door member 300 is free to move to the dispensing position due to the fact that the pin 702 is in the retracted position. When the pin 702 is retracted, it lies below the top portion 310 of the door member 300 and therefore, the door member 300 can freely rotate to the degree permitted by the tabs 910, 1010 within the slots 313, 315. The lengths of the slots 313, 315 thus ultimately determine the degree of permitted travel of the door member 300. The door portion 320 is free to move a sufficient distance within the recessed track 220 such that the medication dispensing opening (window) 215 is open. There is a limit to the clockwise movement of the door member 300 due to the tab 1010 being constrained within the slot 315 of the door member 300.

Figure 9:
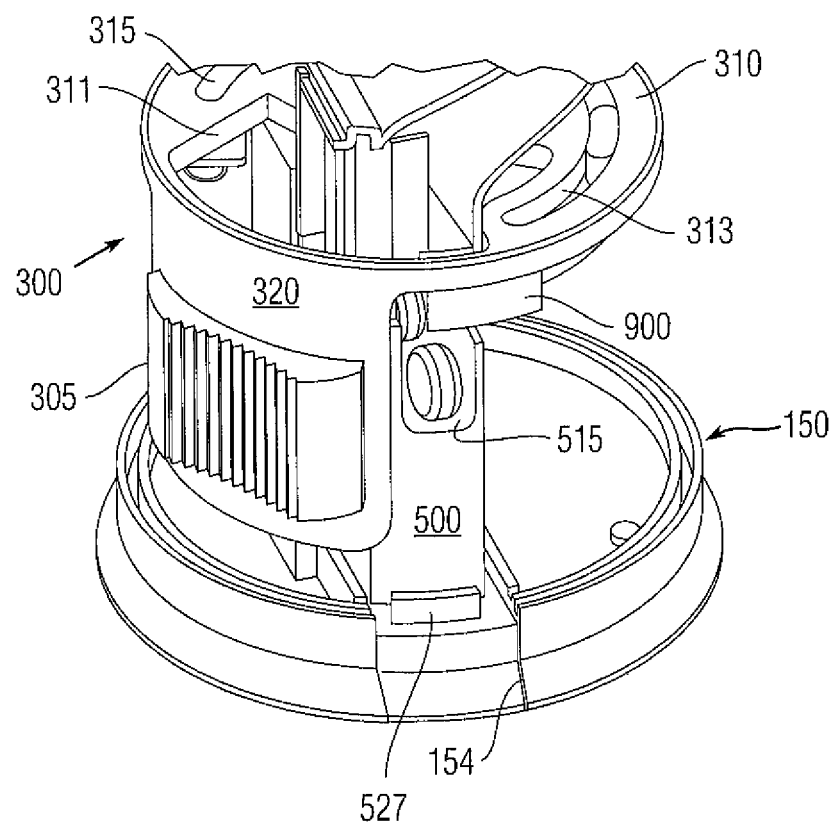
FIG. 9 is a side perspective view of the door member and the pill dispensing mechanism in a dispensing position.

As the door portion 320 becomes laterally offset from the window 215, the pill in the dispensing position of the U-shaped slot 315 (i.e., the bottommost section of the U-shaped slot 315) exits the device 100 and is received by the patient. As mentioned above, when there are additional pills in the bottle 110, the next pill to be dispensed (i.e., in a pre-load position) is captured between the second end 904 of the plunger member 900 and the first side wall 507. However, in this pre-load position, the pill cannot be dispensed and instead, will not be released until the door member 300 is: (1) first placed into the load position which causes retraction of the plunger member 300 from the insert 100, thereby causing the previously captured pill (that is in the pre-load position) to drop into the dispensing position (i.e., the bottommost location of the U-shaped slot 315) and (2) subsequently placed into dispensing position in which the window 215 is open. These steps result in the next to be dispensed pill dropping into the dispensing location of the U-shaped slot 315 and then the subsequent opening of the pill dispensing window 215 at the appropriate time and when certain pill dispensing criteria have been satisfied. FIGS. 9-10 show the door member 300 in the dispensing position and the release of one pill.

It will be understood that the processor is programmable and the patient's prescription regimen is loaded therein. As is well known, in many prescription regimens, more than one pill is taken at one time (e.g., take 3 pills in the morning and 3 in the evening). The processor and the other parts of the present device 100 are configured so that multiple pills can be released successively to satisfy the patient's prescription regimen. For example, the processor monitors and records each dispensing action and therefore, when it is the appropriate time to release multiple medications to the patient, the processor permits successive loading and dispensing actions up to the number required to dispense the medication. For example, to dispense three pills, the processor permits three successive door opening actions within allotted pill dispensing time period.

It will also be appreciated that the device 100 can incorporate visual and/or audio indicators/reminders to alert the user as to the status of the device 100 and in particular, whether it is the appropriate time to dispense a pill. For example, a portion of the base 150 and/or the base portion 525 can be formed of a transparent or semi-transparent material and the device 100 can include one or more lights (e.g., LED) that are activated to illuminate and be visible through at least one of the base 150 and the base portion 525 to indicate the current status of the device 100. For example, when it is an appropriate time for medication to be dispensed, a green light can be visible through the base portion 525 of the insert 500 to visually alert the user that it is time to take medication. Conversely, when it is not time for dispensing medication, the base 150 can be illuminated in another color, such as blue, that indicates to the user that it is not time to take the medication and that the device 100 will not allow such medication dispensing. In this embodiment, the insert 500 is illuminated to alert the user that it is time to take the medication and conversely, the base 150 is illuminated to alert the user that it is not time to take the medication. However, it will be appreciated that other lighting schemes are possible including one in which only the insert 500 or only the base 150 is illuminated in different colors to indicate the status of the device 100. Also, the device 100 can be configured to only illuminate when it is time to take the pill and otherwise will be in a rest, illuminate condition.

It will be appreciated that the visual indicator can either include a solid, illuminated color or can be a blinking color. Since the processor is fully programmable, the alert options are endless in that the device 100 can only illuminate when it is ready to take medication and otherwise, no visual indicator is displayed. Alternatively, the device 100 can always include some visual indicator, as described below.

It will be appreciated that any number of programmable processors can be used and are configured to enter a patient's prescription regimen and to continuously monitor the dispensing actions. For example, the software associated with the processor translates concatenated instructions using signa codes used by pharmacies to translate doctor script instructions into a digital signature that the processor uses to control operation of the device 100. For example, the digital signature can be as follows; however, it will be appreciated that following data is merely exemplary and is not limited to the present invention. The device 100 is a fully programmable device and the processor can be programmed in any number of different ways.

| SIGNA_CODE | LANGUAGE | SIGNA_MESSAGE | DOSAGE_PER_DAY | Time 1 | Time 2 | Time 3 | Time 4 | Time 5 |
|---|---|---|---|---|---|---|---|---|
| 1HS | E | AND 1 AT BEDTIME | 1 | 18:00-02:00 | | | | |
| 2HS | E | AND 2 AT BEDTIME | 2 | 18:00-02:00 | | | | |
| 5D | E | 5 TIMES DAILY | 5 | 06:00-0:00 | 2 h from dose | 2 h from dose | 2 h from dose | 2 h from dose |
| ABR | E | BEFORE BREAKFAST | 1 | 05:00-13:00 | | | | |
| ABS | E | BEFORE BREAKFAST AND SUPPER | 2 | 05:00-13:00 | 17:00-02:00 | | | |
| AC | E | BEFORE MEALS | 3 | 05:00-13:00 | 13:00-17:00 | 17:00-02:00 | | |
| ADIN | E | BEFORE DINNER | 1 | 17:00-02:00 | | | | |
| ALUN | E | BEFORE LUNCH | 1 | 11:00-14:00 | | | | |
| AM | E | IN THE MORNING | 1 | 06:00-12:00 | | | | |
| AMPM | E | MORNING AND EVENING | 2 | 06:00-12:00 | 17:00-02:00 | | | |
| ASUP | E | BEFORE SUPPER | 1 | 17:00-02:00 | | | | |
| ATC | E | AROUND THE CLOCK | 0 | 0:00-23:59 | | | | |
| BCP | E | 1 TAB DAILY FOR 21 DAYS, STOP FOR 7, THEN REPEAT | 1 | 0.00-23:59 | | | | |

The software takes the codes and translates them into a program that is hosted by the processor (i.e., PCB/chip) in the device 100. The PCB/chip (processor) can either sleep while it is in-transit or activates at the time of the first dispense T. The software instructs the mechanical components to allow the load and release of X (number of pills) at T+1, T+2, etc., in which T is the first time the patient takes a pill. The device 100 of the present invention can be configured so as to allow a "casual release" out of schedule by keeping the mechanical handle on the load position for more than X number of seconds (e.g., 20 seconds). The device 100 timestamps each release as either normal or "casual" depending upon the manner the pill was dispensed (dispensing mode).

The device 100 can thus be thought of as a smart cap for use with traditional pill bottles 110 and reminds, facilitates, monitors, and records medication dispensing. The device 100 accounts for every single pill. The device 100 dispenses different kinds of pill. Hence it can be used to monitor multiple medications.

The device 100 can, in one embodiment, has the following characteristics: (1) fits standard pill bottles 110; (2) supports multiple pill sizes and quantities; (3) is easily programmable with the patient's prescription dosages and dose times; (4) provides patient reminders to take the medication; (5) allows the patient to only take the prescribed dosages (with the prescribed dosage time window); (6) monitors that the doses are taken through direct pill counting at the time of dispensing; (7) stores dispensing data and can optionally report this data back to a central monitoring database through a wireless network or some other network, such as a wired network. The wireless network can also be used for medical dispenser cap programming, etc.

As set forth herein, the device 100 is not particularly intended for placement on the pill bottle 110 by the end user, in this case the patient. Instead, the device 100 can be securely and non-removably (under normal operating conditions) attached to a filled pill bottle 110 by a pharmacist or other trained person.

After the patient has taken all of the medication or when it is otherwise time for refilling the prescription, the patient returns the empty combined pill bottle 110 and the device 100. It will be readily apparent whether the patient tampered with the combined pill bottle 110 and device 100 as by removing the emergency tab 1500 or by otherwise damaging the device 100 and/or bottle 110.

The combination pill track and insert assembly provides a means for customizing the pill dispensing device 100 based on specific prescription type of a particular patient. As described herein by incorporating the adjustable pill ramp member 450 as part of the pill dispensing track 410, the dimensions and characteristics and the track 410 can be modified and optimized to ensure that pills are fed properly and that no pill jams or other dispensing malfunctions occur.

Information can be transferred from the device 100 to another device using any number of information protocols, etc. For example, a low power, short range wireless communication system (wireless interface) can be used and the data can be transmitted via broadband, cellular, Bluetooth, wireless protocol, etc. can be used.

Alternatively or concurrently, the casing 200 of the device 100 can include a data port (e.g., USB port) or the like that receives an electronic device, such as a portable memory device that can receive and store in memory the compliance and dispensing information stored in memory in the device 100. A cable or the like can be inserted into the data port to permit data transmission from the device 100 to the other electronic device which can be in the form of a personal computer or the like.

The device 100 can thus be configured to include software that takes the dispensing (compliance) information and communicates it to a central server in which physicians, family, insurance or pharma companies can have access to reports either aggregated by drug-type, etc., depending on who accesses the information. The set up follows strict privacy HIPPA requirements and other applicable rules, etc.

When the device 100 is part of a remote compliance management system 2000, the pull tab 1500 can interface with a sensor or the like that is electronically connected to the processor such that removal of the pull tab 1500 triggers the sensor and causes a signal to delivered to the processor. The processor can then process this alert signal and send a signal (message) to a remote compliance management system 2000 to alert the caretaker (e.g., a physician) that the patient broke the seal between the pill bottle 110 and the device 100. The caretaker can make appropriate inquiry with the patient.

The device 100 and system 2000 can thus be part of a telehealth application in which remote compliance monitoring is possible. In addition, when part of a telehealth application, the status updates can be sent from the device 100 to the system 2000. For example, a physician or the like can monitor data from the device 100 to see if the patient is adhering to the prescription regimen. The processor of the device 100 can be configured such that if the patient misses a drug dispensing time period (i.e., misses a pill), the event is noted and is sent to the remote components of the system 2000. Additional more urgent messages can be delivered to the remote system 2000 from the device 100 if additional pills are not dispensed in additional future dispensing time periods.

FIGS. 13-25 show a medication dispensing device 2100 according to the present invention that can be and is preferably part of the medication compliance system 2000 (FIG. 12). Similar to the device 100, the medication dispensing device 2100 is formed of a number of individual parts that when assembled form the medication dispensing device 2100. In particular, the dispensing device 2100 is in the form of a cap structure that is configured to mate with a conventional pill bottle (not shown but shown in FIG. 1). As discussed below, a secure and non-releasable connection can be formed between the pill bottle and the dispensing device 2100 so as to prevent an individual, such as the patient or another, from tampering with and gaining access to the contents of the pill bottle.

Since the medication dispensing device 2100 is similar to the device 100, similar or identical components are numbered alike. In particular, the device 2100 includes base 150 which is constructed such that when the pill bottle 110 is inverted, the base 150 rests on a support surface and supports the pill bottle 110 in an upstanding position. Along the circumference of the base 150, the notch or opening 154 is formed.

The pill dispensing device 2100 also includes the casing or housing 2110 which securely mates with the base 150. The housing 2110 is very similar to the casing 200 with the differences being discussed below. A secure mechanical attachment, such as a snap-fit type attachment, can be used to attach the casing 2110 to the base 150 as discussed previously. The side wall 206 includes recessed portion or track 220. Within the recessed portion 220 of the side wall 206, the medication (pill) dispensing opening (window) 215 (FIG. 18) is formed. The window 215 is open to the hollow interior of the casing 2110.

The top surface 230 of the casing 2110 includes the first opening or recess 235 that is generally centrally located. In the illustrated embodiment, the recess 235 is a hexagonal shaped recess. The casing 2110 includes the through opening 237 that is in registration with the notch 154 of the base 150 when the casing 2110 and base 150 mate together. This registration permits an object to be passed from the underside of the base 150 through the casing 2110. Unlike the notch 154 that is open along the side of the base 150, the through opening 237 is a completely bounded opening.

The casing 2110 also includes a number of recessed tracks formed therein along and within the top surface 230. More specifically, the top surface 230 includes a first recessed track 2140 that is formed proximate a peripheral edge of the casing 2110 and a second recessed track 2150 that is formed proximate a peripheral edge of the casing 2110. The through opening 237 is located between the recessed tracks 2140, 2150. Each of the first and second recessed tracks 2140, 2150 has an arcuate shape since the track runs along a length of the circumferential peripheral edge of the casing 2110. The first recessed track 2140 is a multi-layer recess in that a center portion 2142 of the track 2140 has a maximum depth and a recessed landing 2144 is formed about the center portion 2142. The landing 2144 is recessed a first distance relative to the top surface 230 and a floor of the center portion 2142 is recessed a second distance relative to the top surface, with the second distance being greater than the first distance.

Similarly, the second recessed track 2150 is a multi-layer recess in that a center portion 2152 of the track 2150 has a maximum depth and a recessed landing 2154 is formed about the center portion 2152. The landing 2154 is recessed a first distance relative to the top surface 230 and a floor of the center portion 2152 is recessed a second distance relative to the top surface, with the second distance being greater than the first distance.

Figure 17:
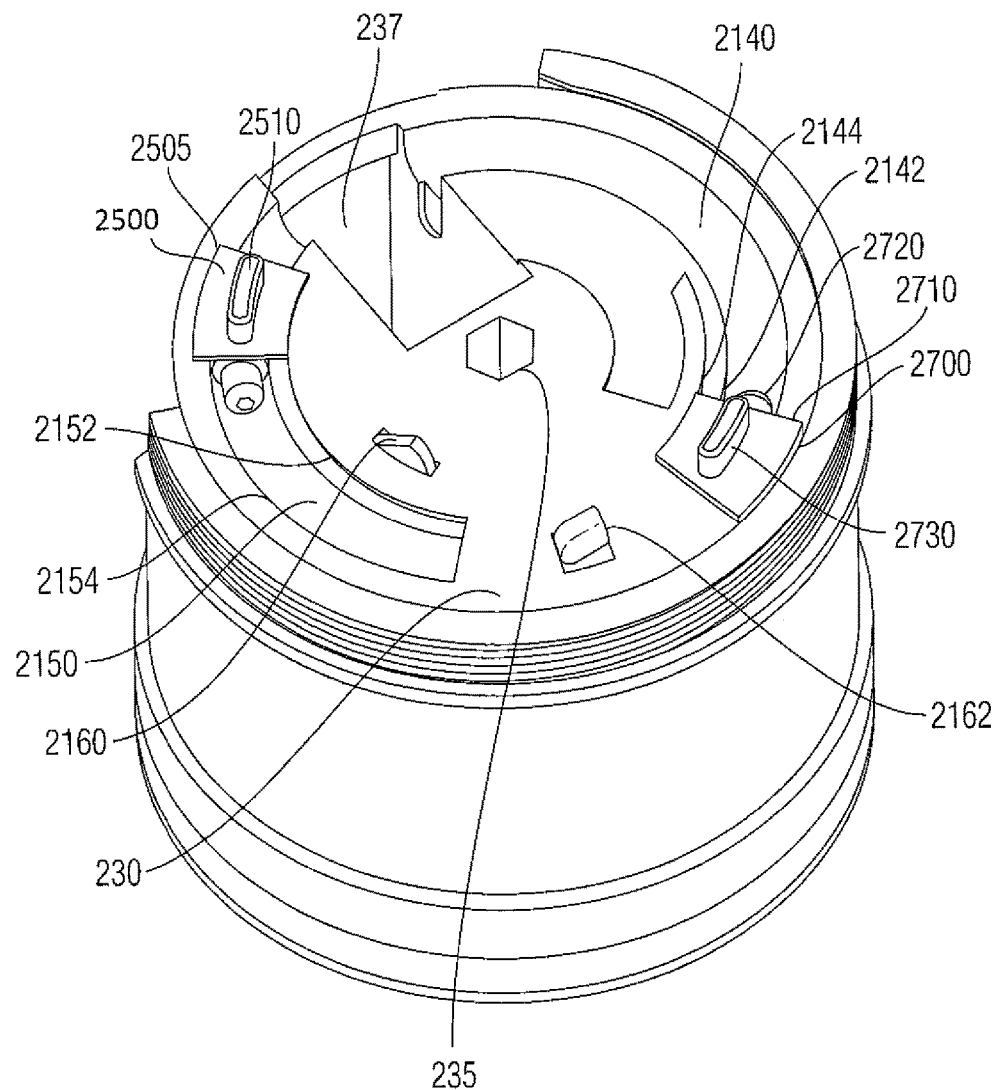
FIG. 17 is a top and side perspective view of the assembled casing and pill door member.
Figure 18:
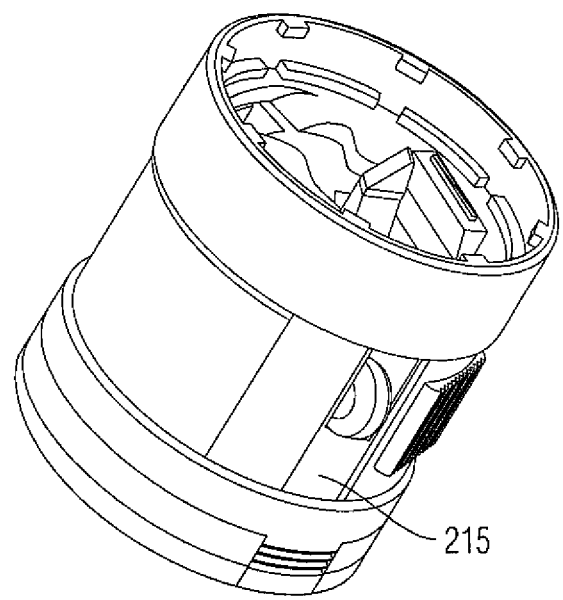
FIG. 18 is a side perspective view of the assembled casing and pill door member in an open position.
Figure 19:
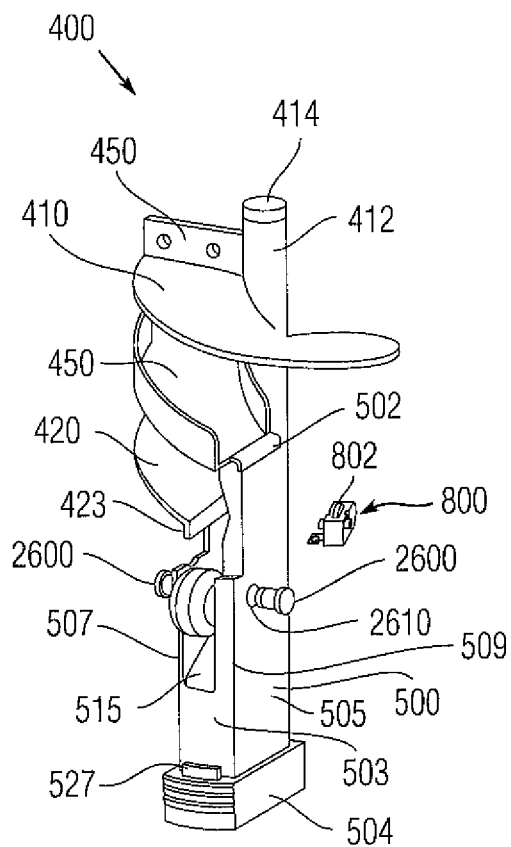
FIG. 19 is a side perspective view of the insert and pill track with detection means.
Figure 20:
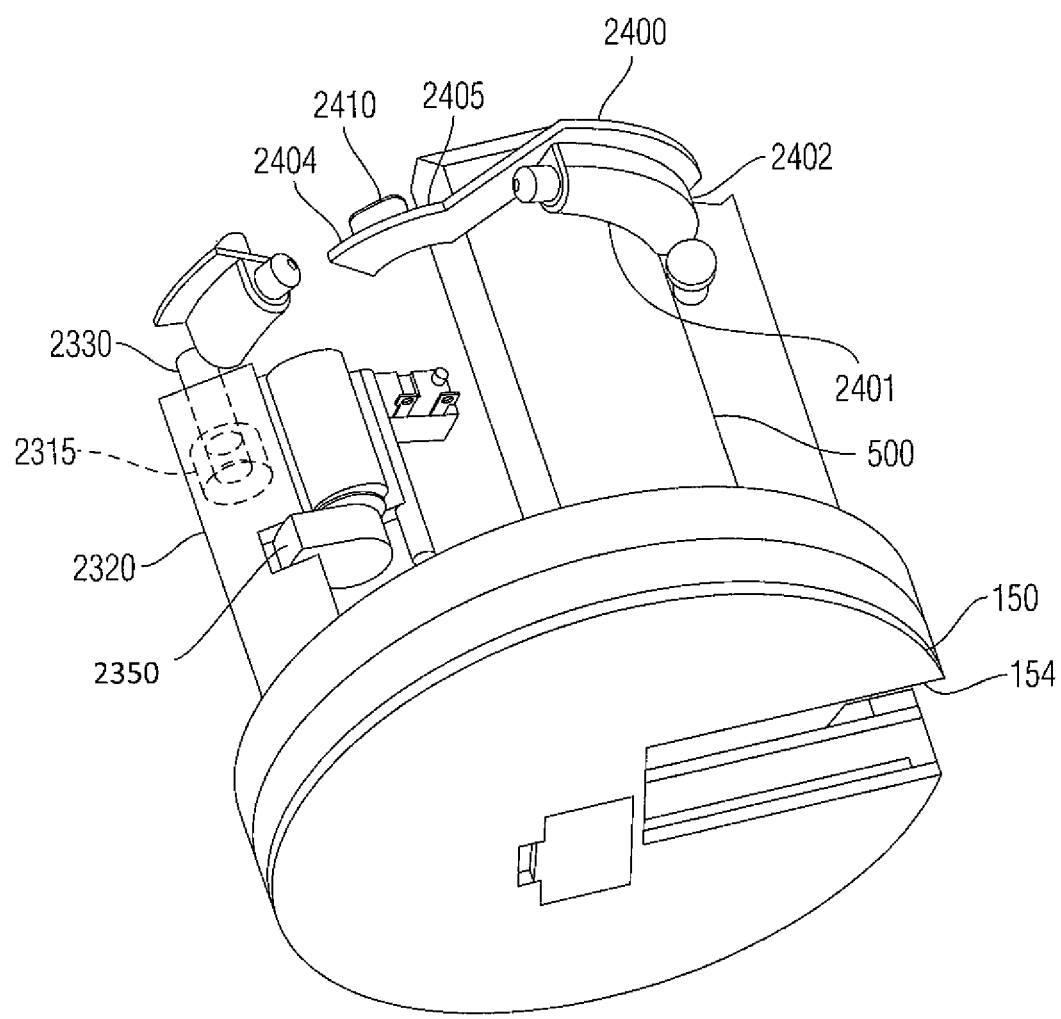
FIG. 20 is a bottom perspective view of the base and other working components including a controllable cam member for selectively limiting the movement of the pill door member.
Figure 21:
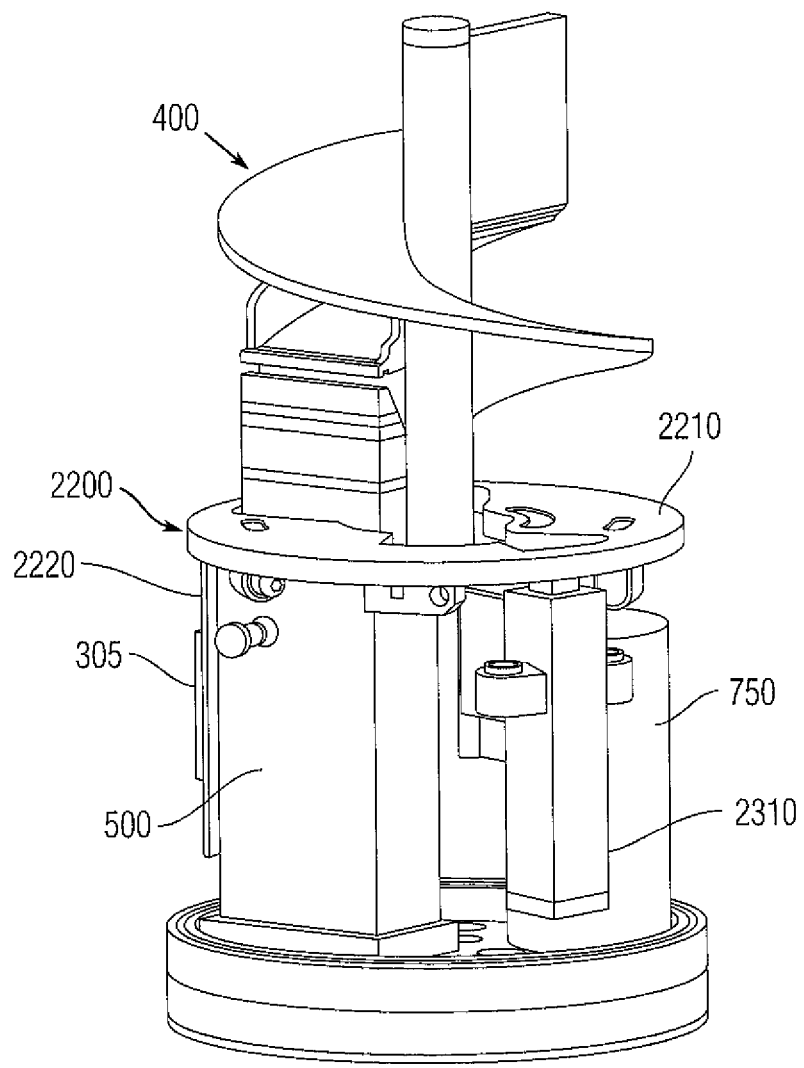
FIG. 21 is a side perspective view of the base and other working components including a controllable cam member.

The length of the second recessed track 2150 is less than the distance of the first recessed track 2140. As shown in FIG. 17, the first and second recessed tracks 2140, 2150 are generally opposite one another. While the first recessed track 2140 is open to the through opening 237, the second recessed track 2150 is not open to the through opening 237 and terminates at a location spaced therefrom.

The casing 2110 also includes a second through opening 2160 that is formed therein and is open along the top surface 230. The second through opening 2160 is located between the second recessed track 2150 and the recess 235. The casing 2110 also includes a third through opening 2162 that is formed therein and is open along the top surface 230. The third through opening 2162 is formed between the first and second recessed tracks 2140, 2150 generally opposite the through opening 237.

Between the assembled casing 2110 and the base 150, a number of working components are contained within the hollow interior spaces. For example, a power source and electronic components of the device 100 can be stored and operatively connected to the working components of the device 100 as described below.

The device 2100 also includes a movable (slidable) door member 2200 that mates with the casing 2110 and selectively allow opening of the window 215. The door member 2200 is similar to the door member 300 and therefore, mainly the differences are discussed in more detail. The door member 2200 includes a top portion 2210 that seats against the top surface 230 of the casing 2110 and a door portion 2220 that extends downwardly form the top portion 310. As shown in the figures, the top portion 2210 is in the form of an annular shaped disk-like structure and the door portion 2220 is in the form of an arcuate shaped tab that is designed to travel within the recessed portion or track 220 and cover the window 215. The door portion 2220 is formed at a right angle to the top portion 2210 and thus represents a vertical portion, while the top portion 2220 represents a horizontal portion.

The top portion 2210 is substantially hollow and in particular, the top portion 2210 includes a main through opening or slot 2211 and an arcuate shaped opening or slot 2213 and a second opening or slot 2215, which are located opposite one another across the main opening 2211. The slots 2213, 2215 are through openings. The slot 2213 is intended for placement over the recessed track 2150 and the slot 2215 is for placement over the recessed track 2140. The top portion 2210 also includes an opening 2217 that is located between the peripheral edge and the opening 2215 adjacent an open section of the main slot 2211.

The disk-shaped top portion 2210 has a complementary shape relative to the casing and therefore, can be a circular shaped disk that rests on the top surface 230 of the casing 2110. The diameter of the disk-shaped top portion 2210 is selected so as to not extend over the threads at the top end of the casing. In addition, the door portion 2220 is received within the opening (arcuate slot) formed between the recessed track 220 and the threads that extend across the top edge of the recessed track 220. In this manner, the disk-shaped top portion 2210 can seat against and be supported by the top surface 230 while the door portion 2220 is disposed within the recessed track 220 in such a way that the disk-shaped top portion 2210 can freely rotate on the top surface 230 and the door portion 2220 can slidingly travel within the recessed track 220.

A thumb grip member 305 is attached to the door portion 2220 to provide a rough surface that is configured to receive a thumb or finger of the patient or individual for laterally sliding the door portion 2220 within the recessed track 220. The thumb grip member 305 attaches to the door portion 2220 using traditional techniques, such as a mechanical attachment, e.g., a snap fit.

The recessed track 220 defines two door positions at either end thereof and in particular, the at one end of the track 220 is a door lock position in which medication cannot be dispensed and at another end is a medication release position. The door portion 2220 is sized and designed to cover the pill dispensing window 215 except for when the door member 2200 is permitted to move into the medication release position as described herein. In the normal rest position, the door portion 2220 is disposed over the medication dispensing window 215 and therefore, the medication is prevented from being dispensed. Conversely, when the door portion 2220 is in the medication release position, the door portion 2220 is offset from the medication dispensing window 215 and therefore, the medication is free to be dispensed as described herein. The degree of travel of the door portion 2220 within the recessed track 220 is limited and defined by the end walls/edges of the recessed track 220. In other words, when the door portion 2220 abuts one end wall of the recessed track 220, the door portion 2220 has reached one end of travel and when the door portion 2220 abuts the other end wall of the recessed track 220, the door portion 2220 has reached the other end of travel.

Similar or identical to the device 100, the device 2100 also includes the pill track and dispenser assembly 400 that is at least partially selected in view of the type of pill that is contained in the pill bottle. The pill track and dispenser assembly 400 includes two main parts, namely, the pill track member 410 and the insert 500 that mates with the pill track 410 and configures the pill track 410 to have a desired orientation that allows the pills to only travel when they lie horizontal as opposed to lying vertically (i.e., on their sides). Both the pill track member 410 and the insert 500 have been previously described in great detail with respect to the embodiment of the device 100 and therefore, these parts are not described in detail again but instead the like components are numbered alike in the present drawings. However, any differences between the two embodiments are highlighted below.

As shown in the figures, the insert 500 passes through the main slot 2211 formed in the top portion 2210 of the door member 2200. The insert 500 is stationary; however, the shape of the main slot 2211 is configured to permit a degree of rotation of the top portion 2210 above the casing 2110 before interference between the door member 2200 and the insert 500.

The construction and features of the insert 500 and the pill track member 410 are described in detail hereinbefore with reference to a previous embodiment.

The main slot 2211 has an irregular shape in that it is narrower at one end and is wider at an opposite end (180 degrees away). In addition, the top portion 2210 is formed such that it includes a cam surface 2219 that is located adjacent the main slot 2211 and is angled downwardly into the opening of the main slot 2211. The cam surface 2219 thus resembles a beveled surface.

The device 2100 also includes a controllable pill release mechanism 2300. The pill release mechanism 2300 includes both mechanical and electronic features and in particular, the pill release mechanism 2300 includes an actuator unit 2310 (FIGS. 20-21) that permits controlled movement of the door member 2200 relative to the casing 2110 so as to open the drug dispensing window (opening 215) under select conditions to allow dispensing of a pill. The electronic components further include a power source 750 that can be in the form of a battery that is stored within the hollow interior of the casing 2110 and a processor, such as a printed circuit board, that is electrically connected to the power source 750 and the actuator unit 2310 for powering and controlling operation of the actuator unit 2310.

Figure 24:
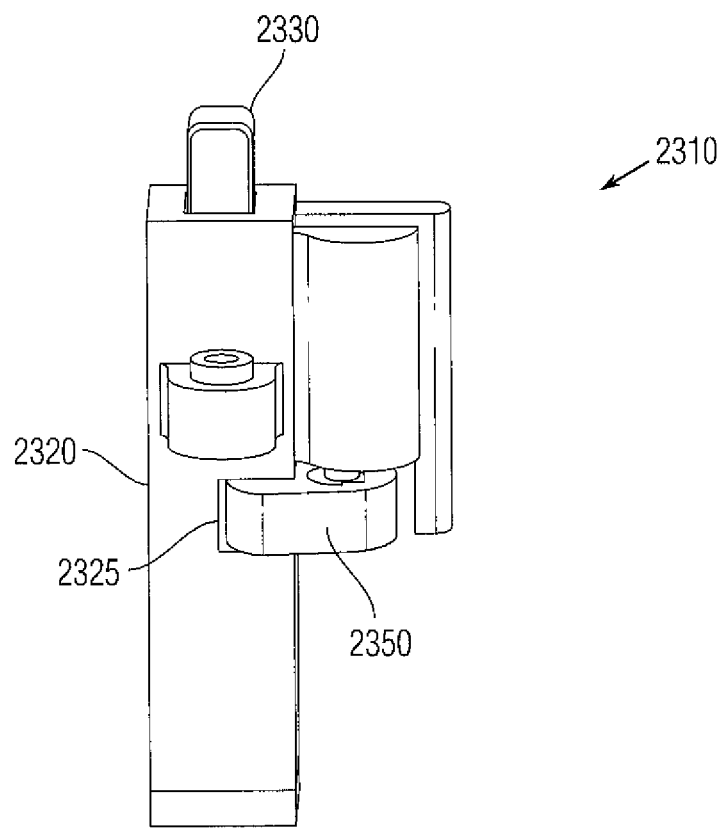
FIG. 24 is a side elevation view of the cam member in a first position.
Figure 25:
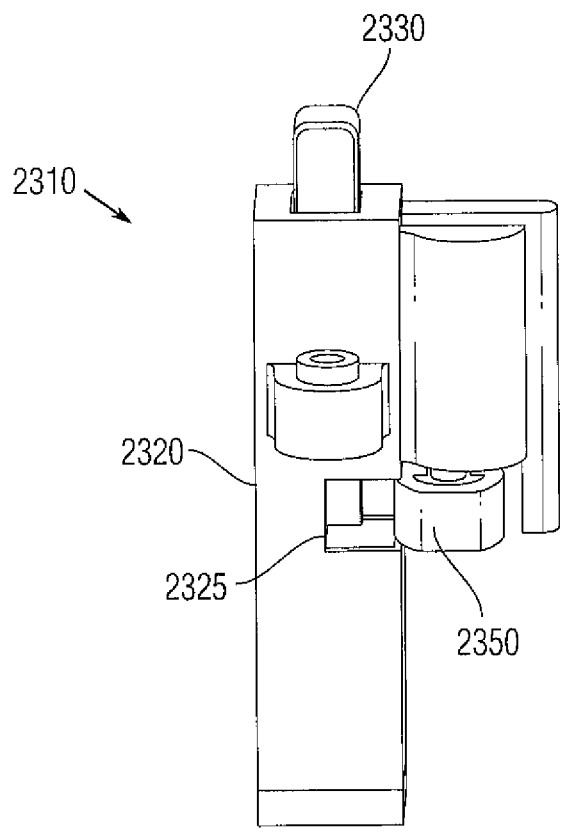
FIG. 25 is a side elevation view of the cam member in a second position.

As shown best in FIGS. 20-25, the actuator unit 2310 is a cam based mechanism that is defined by an elongated actuator body 2320 that has a top end that is disposed proximate the underside of the top portion 2210 of the door member 2200 and an opposite bottom end that faces the base. The actuator unit 2310 includes a biased pin or protrusion 2330 that protrudes outwardly from the top end and travels within a channel or bore formed in the body 2320. The pin 2330 is sized and shaped so as to be received within the opening (slot) 2162 and in particular, in the normal extended position, the pin 2330 extends through the opening 2162 and is disposed above the top surface 230 of the casing 2110. As shown in FIGS. 24-25, the pin 2330 has rounded edges that cooperate with the cam surface 2219 as described below.

The biasing of the pin 2330 can be caused by any number of suitable members, including a spring 2315 or the like. The biasing member 2315 applies a force to the pin 2330 such that in the normal rest position, the pin 2330 assumes the fully extended position and extends above the top surface 230 of the casing 2110.

The body 2320 of the actuator unit 2310 has a notch 2325 formed therein below the biasing member 2315 but in registration with the bore in which the pin 2330 travels. In particular, when the pin 2330 is in a retracted position, at least a portion (the lower portion) of the pin 2330 is located within the notch 2325.

The actuator unit 2310 includes a controllable cam member 2350 that moves between a first position and a second position. The cam member 2350 is connected to a drive source, such as a motor, that is carried on the actuator unit 2310. In other words, the source that drives the movement of the cam member 2350 is located on and is part of the unit 2310. The cam member 2350 is a wedge like structure that is sized and shaped to be received within the notch 2325. It will be appreciated that in the first position (FIG. 25), the cam member 2350 is received within the notch 2325 and thereby closes off the channel (bore) in which the pin 2330 travels. Thus, when the cam member 2350 is received within the notch 2325, the pin 2330 is prevented from any downward movement and thus, the pin 2330 is locked in the fully extended position (it extends above the top surface 230 and is received within the main opening (slot) 2211. Thus, when the pin 2330 is in the locked fully extended position, the pin 2330 height and reception within the slot 2211 prevents free full rotation of the door member 2200 and instead, the fully extended position of the pin 2330 restricts rotation of the door member 2200 due to the interference formed between the edge(s) of the main slot 2211 and the pin 2330.

In contrast, when the cam member 2350 is driven to the second position in which it is not within the notch 2325 (FIG. 24), the pin 2330 can travel downward within the channel through the notch 2325. The pin 2330 can thus be depressed downward within the body of the actuator unit. In this depressed position, the pin 2330 lies below the top part 2210 of the door member 2200 and thus, the door member 2200 can freely rotate relative to the casing 2210 since there is no interference between the pin 2330 and the door member 2200.

In the normal operating position, the cam member 2350 is driven to the first position in which it is received within the notch to prevent the pin 2330 from downward movement and thus also prevent free rotation of the door member 2200.

The actuator unit 2310 is disposed within the hollow interior of the casing 2110 and is supported therein by being mounted to surrounding structure(s) using conventional mounting techniques. As mentioned above, the actuator unit 2310 is operatively connected to the power supply 750 and also is connected to the programmable controller (PCB).

Figure 22:
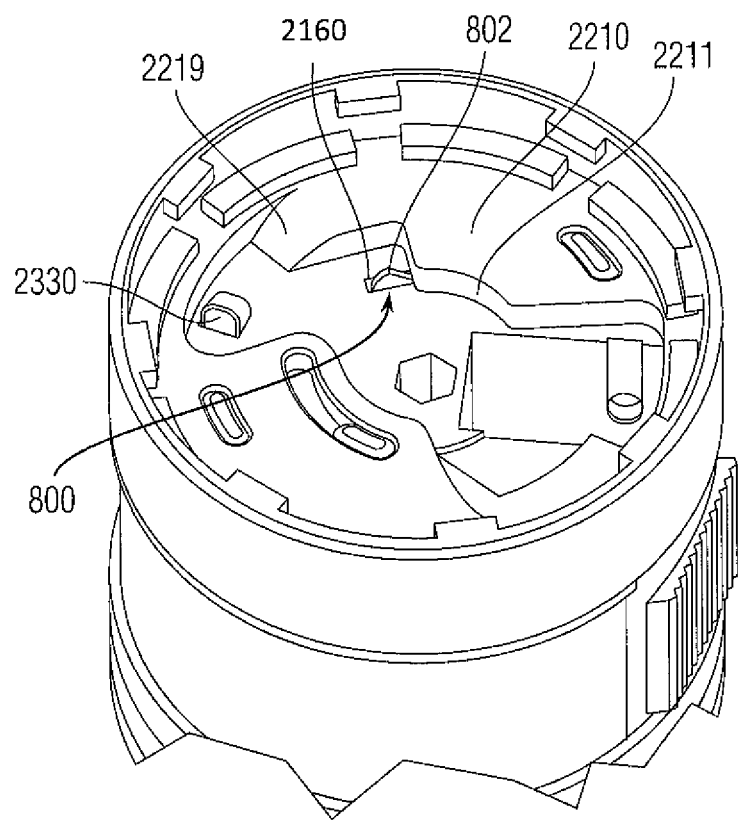
FIG. 22 is a top view of the assembled pill door member and the casing.
Figure 23:
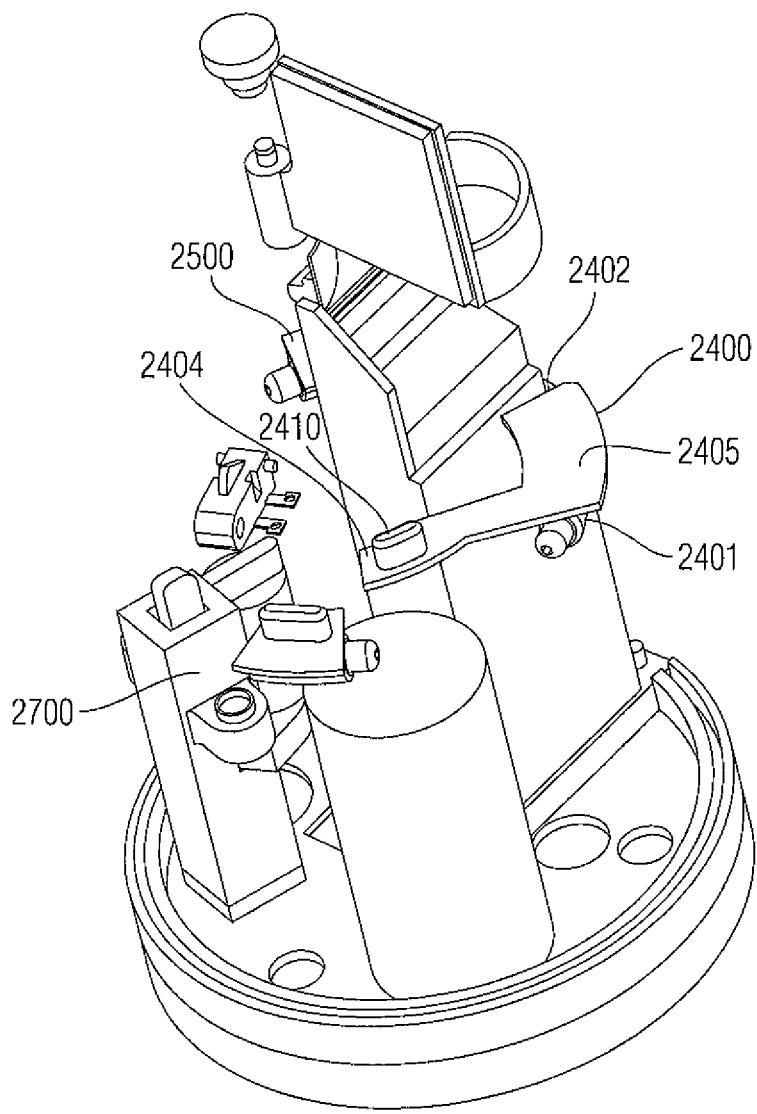
FIG. 23 is a top view of internal components disposed within the casing.

The device 2100 also includes a switch 800 that is disposed within the through opening 2160 and therefore is open and in communication with the door member 2200 is select positions of the top portion 2210. The switch 800 can be in the form of a rocker switch that includes a pivotable portion 802 which has a downwardly sloped top surface that faces the edge of the main slot 2211 (FIG. 22). The pivotable portion faces the top portion 2210 and movement of the top portion 2210 over the casing 200 causes the switch 800 to move between open and closed positions. In particular, when the main opening 2211 of the top portion 2210 lies above the rocket switch 800, the pivotable portion thereof is free to assume the open position since the top portion 2210 does not provide interference. As the door member 2200 is operated, as described below for loading and dispensing the medication, the top portion 2210 is rotated into contact with the pivotable portion 802 of the switch 800 and causes a closing thereof. In particular, during normal operation of the door member 2200, the door member 2200 is rotated counterclockwise and this causes the edge of the top portion 2210 to be driven into contact with the pivotable portion 802 of the switch 800.

When the pivotable portion 802 is compressed and the switch assumes a closed position, the switch 800 sends a control signal to the processor. It will be appreciated that as shown in FIG. 22, the edge of the top portion 2211 contacts the top portion 802 of the switch 800 prior to the cam surface 2219 contacting the pin 2330. Thus, the switch 800 is operated prior to contact between the pin 2330 and the door member 2200 (top portion 2211 thereof).

The controllable pill release mechanism also includes a plunger member 2400 that is designed to control the loading and dispensing of the pills through the pill dispensing window 215. The plunger member 2400 is an arcuate shaped member that is disposed and has a degree of travel within the recessed track 2140. The plunger member 2400 has a first end 2402 and an opposing second end 2404. The plunger member 2400 also includes a top surface 2405 that includes protrusion or tab 2410 extending upwardly from the top surface 2405 near the second end 2404. The plunger member 2400 also includes a bottom portion 2401 that is received within the center portion 2142, while the remaining portion is disposed on the landing 2144. The arcuate shape of the plunger member 2400 is complementary to the arcuate shape of the first recessed track 2140 and therefore can move therein. The first end 2402 can be a flat end. When the plunger 2400 is disposed within the track 2140, the first end 2402 faces the opening 237 and in fact, since the track 2140 is directly open to and forms an entrance to the opening 237, the first end 2402 can be at least partially travel into the opening 237.

The plunger member 2400 is thus coupled to the casing 2110 by having a portion captured within the center portion 2142 of the first recessed channel 2140 and to the top portion 2210 of the door member 2200 as a result of the tab 2410 being received within the arcuate shaped slot 2215 of the top portion 2210. The plunger member 2400 is biased such that it normally assumes an open position in which the first 2402 of the plunger member 2400 is not disextends into the U-shaped slot 515 into either contact with one pill or against the first side wall (whereby the plunger member 900 extends completely across the U-shaped slot 515) due to the first recessed channel 2140 being freely open to the insert 500. The plunger member 2400 is biased using a biasing member, such as a spring that can be captured within the center portion 2142. The biasing member thus biases the plunger member 2400 to the closed position in that the plunger member 900 is driven toward the insert 500 and toward the U-shaped slot 515 for controlling movement of the pills by selectively pinching one pill.

Unlike the previous embodiment, the plunger member 2400 in this embodiment is configured such that the plunger member 2400 is retracted when the door member 2200 is closed so as to allow pills to travel into the U-shaped slot 515. In converse, when the door member 2200 is moved to a released position to dispense a pill, the plunger member 2400 is moved into the position shown in FIG. 16 whereby the edge 2402 of the plunger 2400 is disposed at least partially within the slot 515 to prevent multiple pills from being dispensed. In particular, the edge 2402 pinches the next-in-line pill and thereby only allows the pill that lies in the bottom of the slot 515 to be released. In other words, the plunger 2400 is positioned such that the plunger 2400 (first end 2402) is driven to the slot 515 at a location above the pill to be released and therefore, the plunger 2400 pinches the next-in-line pill. This interference prevents multiple pills from being released and instead controls the dispensing of pills.

Besides the tab 2410, the plunger member 2400 is disposed below the top portion 2210 of the door member 2200. The plunger member 2400 is thus a passive member that is captured by the door member 2200 by means of the tab 2410 being contained in the slot 2215 and therefore, rotation of the door member 2200 causes movement of the plunger member 2400 within the first recessed channel 2140. When the door member 2200 is moved counterclockwise to release a pill, the movement of the door member 2200 causes the tab 2410 to move counterclockwise, thereby causing the biasing member to store energy. When the user releases the door member 2200, the biasing member releases its energy and the plunger member 2400 is driven away from the insert 500 to a position where the plunger member 2400 is not within the slot 515. In other words, when the door member 2200 is moved counterclockwise to release the pill, a force is applied to the plunger 2400 to cause the plunger to be driven at least partially into the slot 515 for pinching the next-in-line pill to prevent that pill from being released and limiting the release to one pill. When the door member 2200 is released, the biasing member releases energy and the plunger is driven away from the slot 515, thereby opening the slot 515 when the door member is in the closed position.

The controllable pill release mechanism also includes a door return member 2500. The door return member 2500 has an arcuate shape member that is disposed and has a degree of travel within the second recessed track 2150. The door return member 2500 includes a top surface 2505 that includes protrusion or tab 2510 extending upwardly from the top surface 2505. The door return member 2500 also includes a bottom portion that is received within the center portion 2152, while the remaining portion is disposed on the landing 2154. The arcuate shape of the door return member 2500 is complementary to the arcuate shape of the recessed track 2150 and therefore can move therein.

The door return member 2500 is thus coupled to the casing 2010 by having a portion captured within the center portion 2152 and within the rest of the recessed channel 2150 and to the top portion 2210 of the door member 2200 as a result of the tab 2510 being received within the slot 2213 of the top portion 310. The door return member 2500 is biased such that it normally assumes a closed position in which the door portion 2220 closes the pill dispensing window 215. The door return member 2500 is biased using a biasing member, such as a spring, that can be captured within the center portion 2152. The biasing member thus biases the door return member 2500 to the closed position in that the door return member 2500 is positioned such that the door portion 2220 closes the window 215 by being disposed in front of the window 215 (i.e., door member 2200 is in the idle position).

Besides the tab 2510, the door return member 2500 is disposed below the top portion 2210 of the door member 2200. The door return member 2500 is thus a passive member that is captured by the door member 2200 by means of the tab 2510 being contained in the slot 2213 and therefore, rotation of the door member 2200 causes movement of the plunger member 2500 within the second recessed channel 2150. When the door member 2200 is moved clockwise, the movement of the door member 2200 causes the tab 2510 to move counterclockwise, thereby causing the biasing member (to store energy). When the user releases the door member 2200, the biasing member releases its energy and the door return member 2500 is driven towards the insert 500, thereby causing the door portion 2220 to close.

Thus, the two biasing members associated with the plunger member and the door return member operate on the door member 2200 to position the door portion 2220 in a rest position in which it covers the pill dispensing window 215 formed in the casing side wall. As explained below, the door member 300 can be moved to the drug (pill) dispensing position by rotating the door member 2200 counterclockwise.

It will be appreciated that in this second embodiment, the pill track can be constructed as in the first embodiment to control the orientation of the pills traveling therealong and is not limited to be constructed to cause the pills to travel in a generally horizontal orientation (e.g., pills can travel vertically or diagonally).

It will also be appreciated that instead of having a pill emergency tab, the pill dispensing device of the present invention can include an electronic user activated emergency release feature that allows a pill to be dispensed under select conditions. For example, the device can be constructed and the controller programmed such that when the user holds the door member in a select position (toward one end of the track 220) for a predetermined amount of time (e.g., 5 seconds or more), a sensor or the like senses that the presence of the door member in this position and after the prescribed time period passes, the sensor sends a signal to the controller. Once the controller receives this signal, the controller can instruct the actuator (such as the solenoid or the cam member) to move to a position that allows the door member to move to the dispensing position, thereby allowing one pill to be dispensed.

It will also be understood that the devices described herein can be part of a system in which the end user has the responsibility to place the dispenser cap on the pill container.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A cap for use with a bottle containing a plurality of pills comprising:
   a casing having a pill dispensing opening, the casing being configured to securely attach to the bottle; and
   a pill dispensing track assembly that includes an adjustable pill ramp for delivering pills to the pill dispensing opening, wherein the adjustable pill ramp is adjustable along a longitudinal direction which is a direction in which each pill travels from the bottle to the pill dispensing opening, wherein the adjustable pill ramp is configured to move between a plurality of different pill dispensing positions by moving the adjustable pill ramp along the longitudinal direction, wherein the pill dispensing position of the adjustable pill ramp dictates and defines a size of pills that can travel along the pill ramp and be dispensed through the pill dispensing opening, wherein at least a portion of the adjustable ramp comprises a sloped floor on which the pills travel in a downward direction toward the dispensing outlet and a ceiling spaced from the floor for allowing the pills to travel therebetween, wherein a distance between the floor and the ceiling is variable due to movement of the adjustable pill ramp in the longitudinal direction and the distance is set such that the pills are presorted as the pills travel along the pill ramp such that the pills only travel in series along the sloped floor to the dispensing outlet.

2. The cap of claim 1, wherein the adjustable pill ramp includes a fixed ramp part whose position does not change and a movable ramp part that is coupled to a biasing member so as to permit the movable ramp part to move between the plurality of different pill dispensing positions.

3. The cap of claim 2, wherein the pill dispensing track assembly includes a hollow central shaft to which the fixed ramp part is fixedly attached, while the movable ramp part includes a tab that is coupled to the biasing member which is contained within an interior of the hollow central shaft, the hollow central shaft including a vertical slot through which the tab extends, the vertical slot guiding vertical movement of the movable ramp part to allow the movable ramp part to move between the plurality of different pill dispensing positions.

4. The cap of claim 3, wherein in an initial position, the biasing member applies a biasing force to cause the movable ramp part to be disposed in a lowermost pill dispensing position.

5. The cap of claim 1, further including an insert that includes a pill dispenser slot that receives pills from the pill ramp and is open to the pill dispensing opening, the insert being detachably coupled to the pill ramp and insertable through an opening in the casing for attachment to the pill ramp, wherein a physical characteristic of the insert determines which pill dispensing position is assumed by the adjustable pill ramp.

6. The cap of claim 1, further including a door member coupled to the casing and movable between a closed position and a dispensing position in which the pill dispensing opening is open and only one pill is released at a time as a result of a pill dispensing mechanism which controls pill dispensing from a pill dispensing slot which defines the pill dispensing opening.

7. The cap of claim 6, wherein the pill dispensing mechanism includes a biased movable member that is coupled to the door member such that when the door member is in the closed position, the movable member is in a retracted position relative to the pill dispensing slot and when the door member moves to the dispensing position, the movable member moves into the pill dispensing slot and assumes a position which prevents a next-in-line pill from advancing into a pill dispensing location in the pill dispensing slot and allows only the one pill to be dispensed from the pill dispensing slot.

8. The cap of claim 7, wherein the movable member comprises a biased plunger member that travels within a recessed track and has a first end that contacts one of (1) a side wall that defines the pill dispensing slot and (2) a portion of the next-in-line pill to prevent the next-in-line pill from moving into the pill dispensing location of the pill dispensing slot until the one pill is dispensed and the door member moves back to the closed position.

9. The cap of claim 8, wherein the pill dispensing slot is in communication with the pill ramp and is configured such that multiple pills can be received therein, the multiple pills assuming the same orientation within the pill dispensing slot.

10. The cap of claim 6, further including an actuator that includes a pin that moves between an extended position and a retracted position, wherein in the extended position, the pin creates interference with the door member and prevents the door member from being moved into the dispensing position, the pin assuming the retracted position under select conditions, whereby the door member is free to move to the dispensing position and the pill dispensing opening is open to allow release of one pill.

11. The cap of claim 10, wherein the actuator is a cam assembly including a driven cam member that moves into a notch formed in an actuator body to lock the door member in the closed position, the pin being spring biased and in communication also with the notch such that when the cam member is disposed outside of the notch, the pin is free to be driven downward into the notch, thereby allowing the door member to move to the dispensing position.

12. The cap of claim 3, wherein the adjustable pill ramp has a helical shape that is formed about the central shaft, the movable ramp part being movable between two fixed ramp parts that at least partially overlie one another.

13. The cap of claim 1, further including a pill sensor that is disposed in communication with a pill dispensing slot that includes the pill dispensing opening, the pill sensor being configured to determine a presence of one pill within the pill dispensing slot and determine when the one pill is dispensed.

14. A cap for use with a bottle containing a plurality of pills comprising:
   a casing configured to securely attach to the bottle and represent a cap structure that closes off the bottle;
   a pill dispensing track assembly that is removably coupled to the casing and includes an adjustable pill ramp for delivering pills to a pill dispenser slot from which the pills are dispensed to a user, wherein in a pill dispensing position, the pill ramp is configured such that the pills are ordered and slide along the pill ramp to the pill dispenser slot and the pills enter and are held within the pill dispensing slot; and
   a pill dispenser mechanism that is arranged relative to the pill dispenser slot and configured such that only one pill is dispensed at a time from the pill dispenser slot, wherein the pill dispenser mechanism includes a moveable plunger member which, when in a first position, allows a pill to be released into a dispensing location of the pill dispensing slot, the pill dispensing slot being defined by first and second opposing side walls, the first side wall defining an opening through which the plunger member travels into the pill dispensing slot, and, when in a second position, the moveable plunger member at least partially occupies the pill dispensing slot and prevents a pill from being released.

15. The cap of claim 14, wherein the pill dispensing mechanism comprises a biased element that has a free end that is selectively received within the pill dispenser slot to prevent a next-to-be dispensed pill from moving within the pill dispenser slot until a select event occurs.

16. The cap of claim 15, wherein the biased element comprises a spring biased plunger that has an arcuate shape and travels within a track and the free end comprises an end of the plunger that is biased such that the free end is selectively received within the pill dispenser slot when the one pill is being dispensed.

17. The cap of claim 16, wherein the track has an arcuate shape.

18. The cap of claim 15, further includes a door member movably coupled to the casing and movable between an open position and a closed position, wherein the select event comprises dispensing of the one pill that is disposed in a bottom location of the pill dispenser slot, whereby dispensing of the one pill creates a space for the next-to-be dispensed pill which is permitted to move into the space only once the door member moves to the closed position.

19. The cap of claim 14, further comprising a pill sensor that is configured to detect a presence of the one pill that is within a pill dispensing location of the pill dispenser slot and detect the dispensing of the one pill.

20. The cap of claim 14, wherein the adjustable pill ramp includes a fixed ramp part whose position does not change and a movable ramp part that is coupled to a biasing member so as to permit the movable ramp part to move between the plurality of different pill dispensing positions.

21. The cap of claim 20, wherein in an initial position, the biasing member applies a biasing force to cause the movable ramp part to be disposed in a lowermost pill dispensing position.

22. The cap of claim 20, wherein the adjustable pill ramp has a helical shape that is formed about a central shaft, the movable ramp part being movable between two fixed ramp parts that at least partially overlie one another.

23. The cap of claim 14, wherein the opening is defined between a top edge of the first side wall and the adjustable pill ramp.

24. A dispenser for dispensing a plurality of articles comprising:
   a casing configured to securely attach to an open end of a receptacle holding the plurality of articles;
   a first mechanism that is coupled to the casing and is configured to receive the plurality of articles within the receptacle and position the plurality of articles such that the plurality of articles travel to a dispensing slot in an orderly manner;
   a second mechanism that is arranged relative to the dispensing slot and configured such that only one article can be dispensed at a time from the dispensing slot; and
   a door member coupled to the casing and movable between a closed position and a dispensing position in which the dispensing slot is open and only one article is released at a time as a result of the second mechanism which controls article dispensing from the dispensing slot and is configured such that a next-in-line article assumes a dispensing position in the dispensing slot only when the one article is dispensed and the door member moves back towards the closed position.

25. The dispenser of claim 24, wherein the receptacle comprises a bottle and the plurality of articles comprises a plurality of pills.

26. The dispenser of claim 25, wherein the first mechanism is configured to position the pills in series and the pill dispensing slot that receives the pills is configured such that the received pills assume a stacked orientation when the pills travel into the pill dispensing slot.

27. The dispenser of claim 25, wherein the first mechanism comprises an adjustable pill ramp for delivering the pills to the dispensing slot from which the pills are dispensed to a user.

28. The dispenser of claim 27, wherein the pills are vertically oriented and stacked within the dispensing slot.

29. The dispenser of claim 24, wherein the second mechanism includes a biased member that is movable between a retracted position in which the biased member is disposed outside the dispensing slot and a fully extended position in which a portion of the biased member is disposed within the dispensing slot, the biased member being coupled to and movable with the door member such that when the door member is in the closed position, the biased member is in the retracted position and when the door member is in the dispensing position, the biased member is in the fully extended position and prevents the next-in-line article from assuming the dispensing location.

30. The dispenser of claim 29, wherein the biased member comprises a plunger that contacts one of (1) a side wall that defines the dispensing slot and (2) a portion of the next-in-line article to prevent the next-in-line article from moving into the dispensing location of the dispensing slot until the one article is dispensed and the door member moves back towards the closed position.

31. A method for dispensing pills from a pill dispenser comprising the step of:
   entering a dispensing schedule into memory of a processor associated with the pill dispenser, the pill dispenser further including a timer and the processor is configured to execute the dispensing schedule that includes predefined dispensing conditions for dispensing one pill at a time from the container only when the predefined dispensing conditions are satisfied;

causing the pills to be received within a first mechanism that is part of a cap and is configured to contact and position the pills such that the pills travel to a pill dispensing slot in a pre-ordered manner; and opening a door member when the predefined dispensing conditions are satisfied, the door member being part of the cap to cause dispensing of only one pill at a time from the pill dispensing slot and detecting and recording each time one pill is dispensed from the pill dispensing slot, wherein the door member moves between a closed position in which the one pill in the pill dispensing slot is not accessible and an open position in which the one pill in the pill dispensing slot freely passes through an opening directly defined by the door member in the open position and is dispensed to a user, wherein the door member is operatively coupled to a biased plunger member, that is biased in a direction toward the pill dispensing slot, such that movement of the door member is translated into movement of the biased plunger between a first position in which the biased plunger member allows one pill to be released into a pill dispensing location of the pill dispensing slot and a second position in which the biased plunger member at least partially occupies the pill dispensing slot and prevents a next in line pill from being released to the pill dispensing location.

* * * * *